United States Patent
Yajima et al.

(10) Patent No.: US 9,220,923 B2
(45) Date of Patent: Dec. 29, 2015

(54) ACCELERATED PARTICLE IRRADIATION EQUIPMENT

(75) Inventors: Satoru Yajima, Niihama (JP); Toshiki Tachikawa, Niihama (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 13/038,853

(22) Filed: Mar. 2, 2011

(65) Prior Publication Data

US 2011/0220809 A1 Sep. 15, 2011

(30) Foreign Application Priority Data

Mar. 9, 2010 (JP) ................................. 2010-052126

(51) Int. Cl.
  *A61N 5/00* (2006.01)
  *A61N 5/10* (2006.01)
(52) U.S. Cl.
  CPC ............ *A61N 5/1081* (2013.01); *A61N 5/1079* (2013.01); *A61N 2005/1087* (2013.01)
(58) Field of Classification Search
  USPC ............ 250/492.1, 492.3, 396 R, 398, 423 R, 250/424
  See application file for complete search history.

(56) References Cited

U.S. PATENT DOCUMENTS

| | | |
|---|---|---|
| 4,917,344 A | 4/1990 | Prechter et al. |
| 5,161,546 A | 11/1992 | Bronn |
| 5,349,198 A | 9/1994 | Takanaka |
| 5,538,494 A | 7/1996 | Matsuda |
| 5,668,371 A | 9/1997 | Deasy et al. |
| 5,695,443 A | 12/1997 | Brent et al. |
| 6,683,318 B1 * | 1/2004 | Haberer et al. ............ 250/492.3 |
| 2003/0163015 A1 | 8/2003 | Yanagisawa et al. |
| 2004/0118081 A1 | 6/2004 | Reimoser et al. |
| 2008/0203323 A1 | 8/2008 | Fehrenbacher et al. |
| 2009/0309046 A1 | 12/2009 | Balakin |

FOREIGN PATENT DOCUMENTS

| | | |
|---|---|---|
| EP | 1 348 465 A1 | 10/2003 |
| EP | 1738798 A2 | 1/2007 |
| EP | 2058027 A1 | 5/2009 |
| JP | 10-071213 A | 3/1998 |
| JP | 2000075100 A | 3/2000 |
| JP | 2001-259058 | 9/2001 |
| JP | 2009502221 A | 1/2009 |

(Continued)

OTHER PUBLICATIONS

European Search Report application No. 11001861.1 dated Jun. 8, 2011.

(Continued)

*Primary Examiner* — Nicole Ippolito
*Assistant Examiner* — Hanway Chang
(74) *Attorney, Agent, or Firm* — Squire Patton Boggs (US) LLP

(57) ABSTRACT

Accelerated particle irradiation equipment is installed in a building having a multi-story structure. The accelerated particle irradiation equipment includes a particle accelerator and an irradiation device. The particle accelerator generates accelerated particles. The irradiation device performs irradiation of the accelerated particles generated by the particle accelerator, and is installed on at least one of the floor above and the floor below the floor on which the particle accelerator is installed.

7 Claims, 23 Drawing Sheets

(56) References Cited

FOREIGN PATENT DOCUMENTS

| WO | 2007/009786 A1 | 1/2007 |
|---|---|---|
| WO | 2008/116535 A1 | 10/2008 |

OTHER PUBLICATIONS

Japanese Office Action application No. P2010-052126 dated Dec. 20, 2011.

EP International Search Report for EP Application No. 12003949.0-2305, dated Sep. 7, 2012.

"New Two-Room Solution From IBA Will Make Proton Therapy Truly Accessible for More Cancer Patients", URL: http://www.businesswire.com/news/home/20091102006072/en/Two-Room-Solution-IBA-Proton-Therapy-Accessible-Cancer, Nov. 2, 2009, [Publication 1].

"New Two-Room Solution From IBA Will Make Proton Therapy Truly Accessible for More Cancer Patients", URL: http://www.businesswire.com/multimedia/home/20091102006072/en/1874825/Two-Room-Solution-IBA-Proton-Therapy-Accessible-Cancer, Nov. 2, 2009, [Publication 2].

URL: http://mms.businesswire.com/bwapps/mediaserver/ViewMedia?mgid=203353&vid=5&download=1, [Publication 3].

"New Two-Room Solution From IBA Will Make Proton Therapy Truly Accessible for More Cancer Patients ", URL: http://group.iba-worldwide.com/node/1130, http://group.iba-worldwide.com/sites/default/files/pressroom/ProteusNan oEN. pdf2, Nov. 2, 2009, [Publication 4].

European Search Report dated Aug. 21, 2013, issued in Application No. 13020008.2.

European Office Action dated Mar. 28, 2014, for corresponding EP Patent Appln. No. 11001861.1

European Office Action dated Oct. 14, 2014, for corresponding European Patent Application No. 11001816.1.

European Patent Office, Office Action for corresponding Appln. No. 13 020 008.2, Sep. 17, 2015.

U. Amaldi, et al., "The Italian project for a hadrontherapy centre", Nuclear Instruments and Methods in Physics Research A 360 (1995), XP004009273, pp. 297-301.

* cited by examiner

ACCELERATED PARTICLE IRRADIATION EQUIPMENT

RELATED APPLICATION

Priority is claimed to Japanese Patent Application No. 2010-052126, filed Mar. 9, 2010, the entire content of which is incorporated herein by reference.

BACKGROUND

1. Technical Field

The present invention relates to accelerated particle irradiation equipment that includes an irradiation device such as a rotating gantry for radiation therapy.

2. Description of the Related Art

Equipment that performs a cancer treatment by irradiating a patient with accelerated particles such as a proton beam is known. This kind of equipment includes a cyclotron that generates accelerated particles, a rotatable irradiation device (rotating gantry) that irradiates a patient with accelerated particles in an arbitrary direction, and a guide line that guides the accelerated particles generated by the cyclotron to the irradiation device. The rotating gantry is provided with a treatment table on which a patient lies, an irradiation unit that irradiates the patient with accelerated particles, and an introduction line that introduces the accelerated particles guided by the guide line into the irradiation unit.

The irradiation unit is freely rotatable relative to the patient, and various types of introduction line that introduce accelerated particles into the irradiation unit are known. For example, as a first aspect, there is known an introduction line that includes a connection portion that is connected to a guide line on the rotation axis serving as a rotation center of an irradiation unit. The introduction line is curved in a substantially U shape on a plane passing through the rotation axis, and is connected to the irradiation unit. Further, as a second aspect, there is known an introduction line that includes a connection portion that is connected to a guide line on the rotation axis. The introduction line is curved so as to be twisted in the circumferential direction of the rotation axis, and is connected to an irradiation unit.

SUMMARY

According to an embodiment of the invention, there is provided accelerated particle irradiation equipment that is installed in a building having a multi-story structure. The accelerated particle irradiation equipment includes a particle accelerator and an irradiation device. The particle accelerator generates accelerated particles. The irradiation device performs irradiation of the accelerated particles generated by the particle accelerator, and is installed on at least one of upper and lower floors of a floor on which the particle accelerator is installed.

BRIEF DESCRIPTION OF TH DRAWINGS

DETAILED DESCRIPTION

Figure 1:
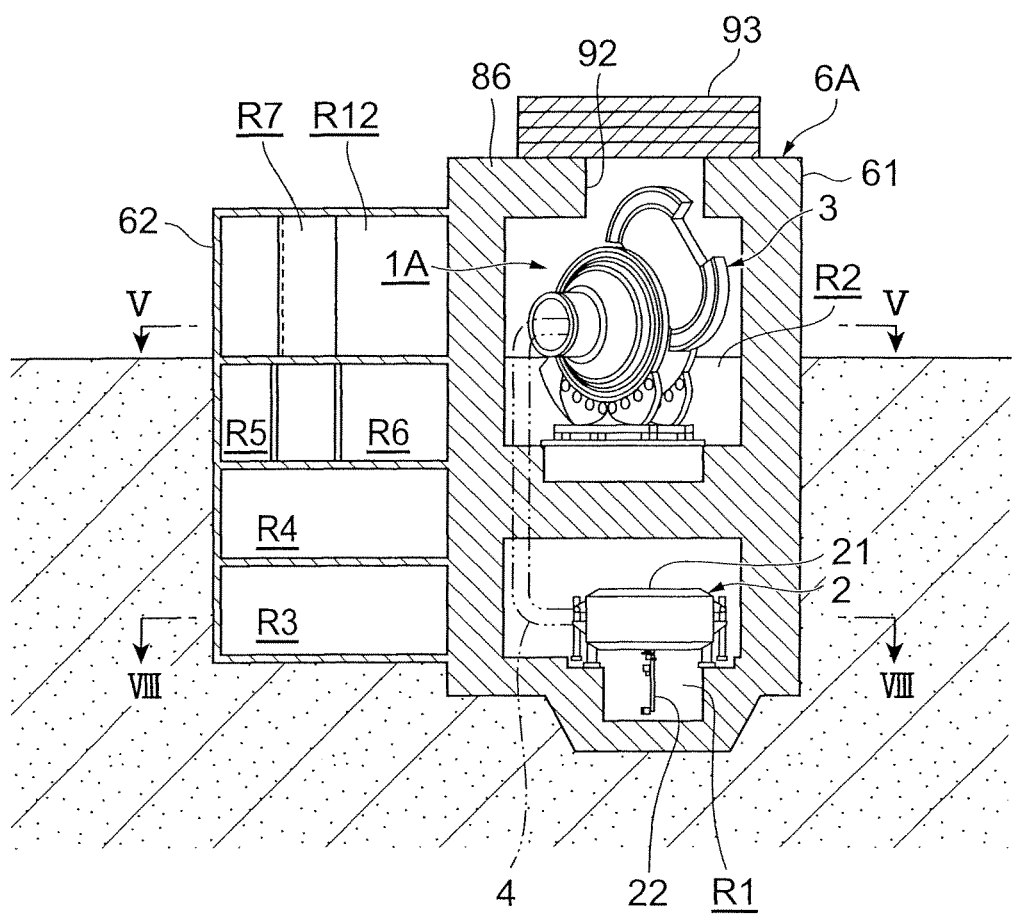
FIG. 1 is a side cross-sectional view of particle radiation therapy equipment according to a first embodiment of the invention.

However, in the equipment in the related art, the cyclotron and the irradiation device such as a rotating gantry have generally been disposed on the same floor. Accordingly, an increase in the size of the facility is caused. For this reason, a large site area is required and it has been difficult to install the equipment in urban areas.

It is desirable to provide accelerated particle irradiation equipment for which the particle accelerator and the irradiation device can be efficiently installed at a predetermined site.

According to the embodiment of the invention, the particle accelerator and the irradiation device are installed on different floors of the building, respectively. Accordingly, it may be possible to reduce as far as possible the installation area occupied by the equipment, for example, by installing the irradiation device immediately above the particle accelerator. As a result, it is easy to efficiently install the particle accelerator and the irradiation device at a predetermined site.

Further, the particle accelerator may be installed on the bottom floor of the building. According to this structure, it may be possible to appropriately install an irradiation device on the upper floor of the irradiation device, which has been already installed, without moving the particle accelerator when the number of irradiation devices is to be increased or the like. Accordingly, it is easy to increase the number of irradiation devices.

Furthermore, the irradiation device may include a rotating unit that is rotatable about a rotation axis, and an irradiation unit which irradiates an irradiation target with accelerated particles generated by the particle accelerator and for which the irradiation direction is changed as the rotating unit is rotated. The irradiation device may be formed in a thin shape so that the length of the irradiation device in the direction of the rotation axis is smaller than the maximum width of the irradiation device in a direction orthogonal to the rotation axis. If the irradiation device is formed in a thin shape, the irradiation device is effective in allowing the reduction of the size of a facility. Therefore, it is easy to efficiently install the particle accelerator and the irradiation device at a predetermined site.

In addition, the accelerated particle irradiation equipment may include a plurality of irradiation devices, and the plurality of irradiation devices may be installed on different floors of the building, respectively. Even when a plurality of irradiation devices needs to be installed, it may be possible to install the plurality of irradiation devices so that the irradiation devices are arranged in line in the up-down direction in accordance with the site area. Accordingly, it is easy to efficiently install the plurality of irradiation devices at a predetermined site.

Moreover, the accelerated particle irradiation equipment may further include a guide line that is connected to the plurality of irradiation devices and the particle accelerator and guides the accelerated particles generated by the particle accelerator to the plurality of irradiation devices, respectively. The guide line may include a take-off path that is connected to the particle accelerator, and a plurality of branched paths that is branched from the take-off path and is connected to the irradiation devices, respectively. The take-off path and the branched paths may be disposed on the same virtual plane. The accelerated particles generated by the particle accelerator are guided by the guide line and are introduced to the irradiation devices, respectively. The accelerated particles trace a predetermined track along the guide line, but need to trace a predetermined curved track at the respective branched paths in order to reach the plurality of irradiation devices, respectively. Here, if the track of the accelerated particles is disposed two-dimensionally on the same virtual plane, it is easy to maintain the symmetry of the track of the accelerated particles. However, if the track of the accelerated particles is deviated three-dimensionally, it is difficult to perform the adjustment for maintaining the symmetry of the track of the accelerated particles. According to this structure, the take-off path and the plurality of branched paths are disposed on the same virtual plane. Accordingly, it is easy to maintain the symmetry of the track of the accelerated particles and the accelerated particle irradiation equipment is effective in improving the accuracy of irradiation.

Further, the accelerated particle irradiation equipment may include a plurality of irradiation devices, and the plurality of irradiation devices may be installed so as to be deviated in a horizontal direction. According to this structure, since the other irradiation device is not installed immediately above one irradiation device and is installed so as to be deviated from one irradiation device in the horizontal direction, it may be possible to install the other irradiation device while avoiding, for example, the highest portion of one irradiation device. Accordingly, it is easy to reduce the height of the building.

Furthermore, the accelerated particle irradiation equipment may include a plurality of irradiation devices, and the plurality of irradiation devices may be installed on the same floor. According to this structure, the accelerated particle irradiation equipment is effective when the height of the building is not so high and the like.

Moreover, the accelerated particle irradiation equipment may include a plurality of irradiation devices. A part of the plurality of irradiation devices may be rotary irradiation devices each including a rotating unit that is rotatable about a rotation axis and an irradiation unit which irradiates an irradiation target with accelerated particles generated by the particle accelerator and for which the irradiation direction is changed as the rotating unit is rotated, and the other part thereof may be stationary irradiation devices each including an irradiation unit for which the irradiation direction is fixed. It may be possible to separately use the rotary irradiation device and the stationary irradiation device, so that the accelerated particle irradiation equipment is effective for appropriately irradiating a patient with accelerated particles.

According to an embodiment of the invention, it may be possible to efficiently install a particle accelerator and an irradiation device at a predetermined site.

Accelerated particle irradiation equipment according to a preferred embodiment of the invention will be described below with reference to drawings. A case where accelerated particle irradiation equipment is used as particle radiation therapy equipment will be described in this embodiment. The particle radiation therapy equipment is applied to, for example, a cancer treatment, and is an apparatus for irradiating a tumor (irradiation target), which exists in a patient's body, with a proton beam (accelerated particles).

As shown in FIG. 1, the particle radiation therapy equipment 1A includes a cyclotron (particle accelerator) 2 that generates a proton beam, a rotating gantry (irradiation device) 3 that is rotatable and irradiates a patient with a proton beam in an arbitrary direction, and a guide line 4 that guides the proton beam generated by the cyclotron 2 to the rotating gantry 3. Further, the devices of the particle radiation therapy equipment 1A are disposed in chambers of a building 6A having a multi-story structure, respectively.

Figure 7:
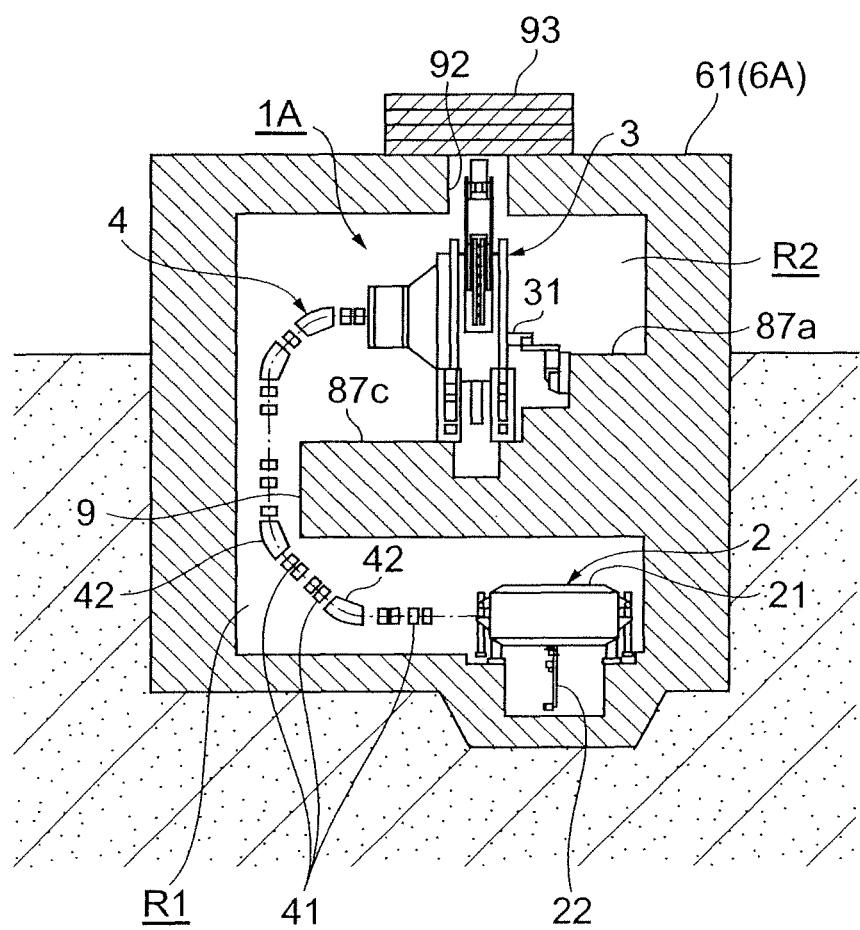
FIG. 7 is a schematic cross-sectional view of the building taken along a line VII-VII of FIG. 5.

A proton beam generated by the cyclotron 2 is guided to the rotating gantry 3 through a track that is formed by the guide line 4. The guide line 4 is provided with quadrupole electromagnets 41 (see FIG. 7) for converging a proton beam and deflecting electromagnets 42 for forming a predetermined track.

The cyclotron 2 includes a vacuum box 21 that accelerates ions therein, and an ion source 22 that supplies ions to the inside of the vacuum box 21. The vacuum box 21 communicates with the guide line 4.

Figure 2:
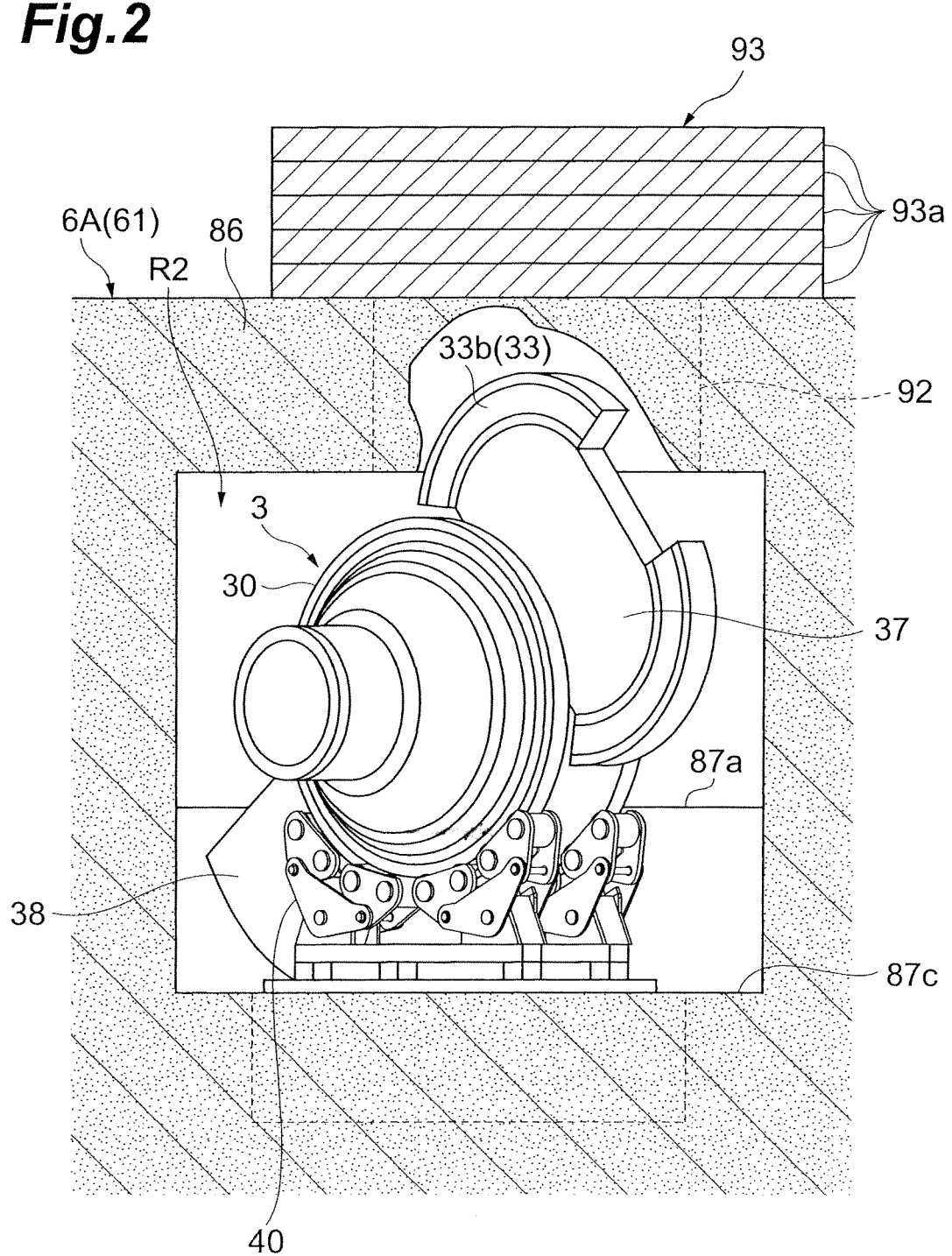
FIG. 2 is an enlarged side cross-sectional view of a gantry chamber.
Figure 3:
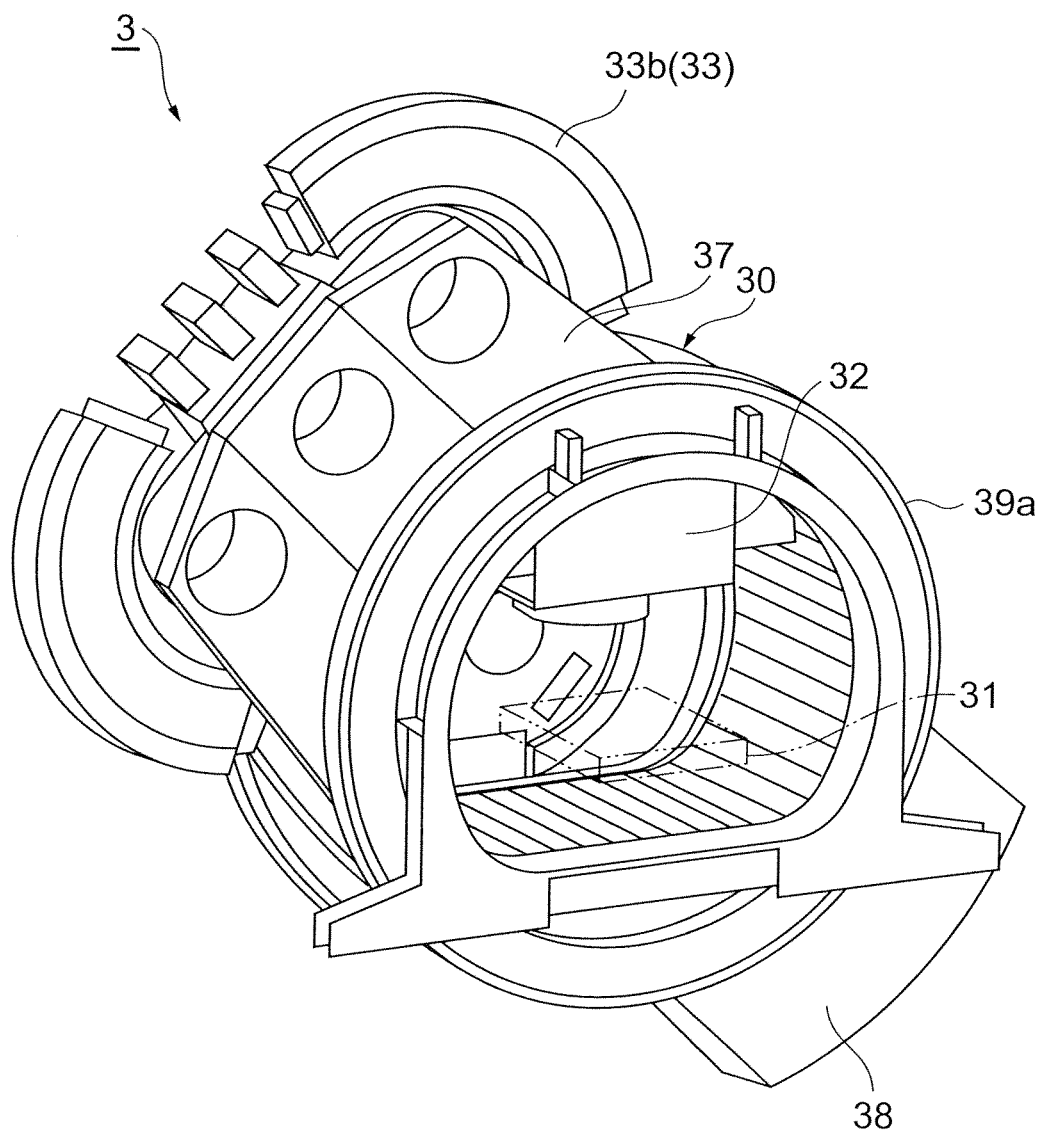
FIG. 3 is a perspective view of a rotating gantry according to this embodiment.
Figure 4:
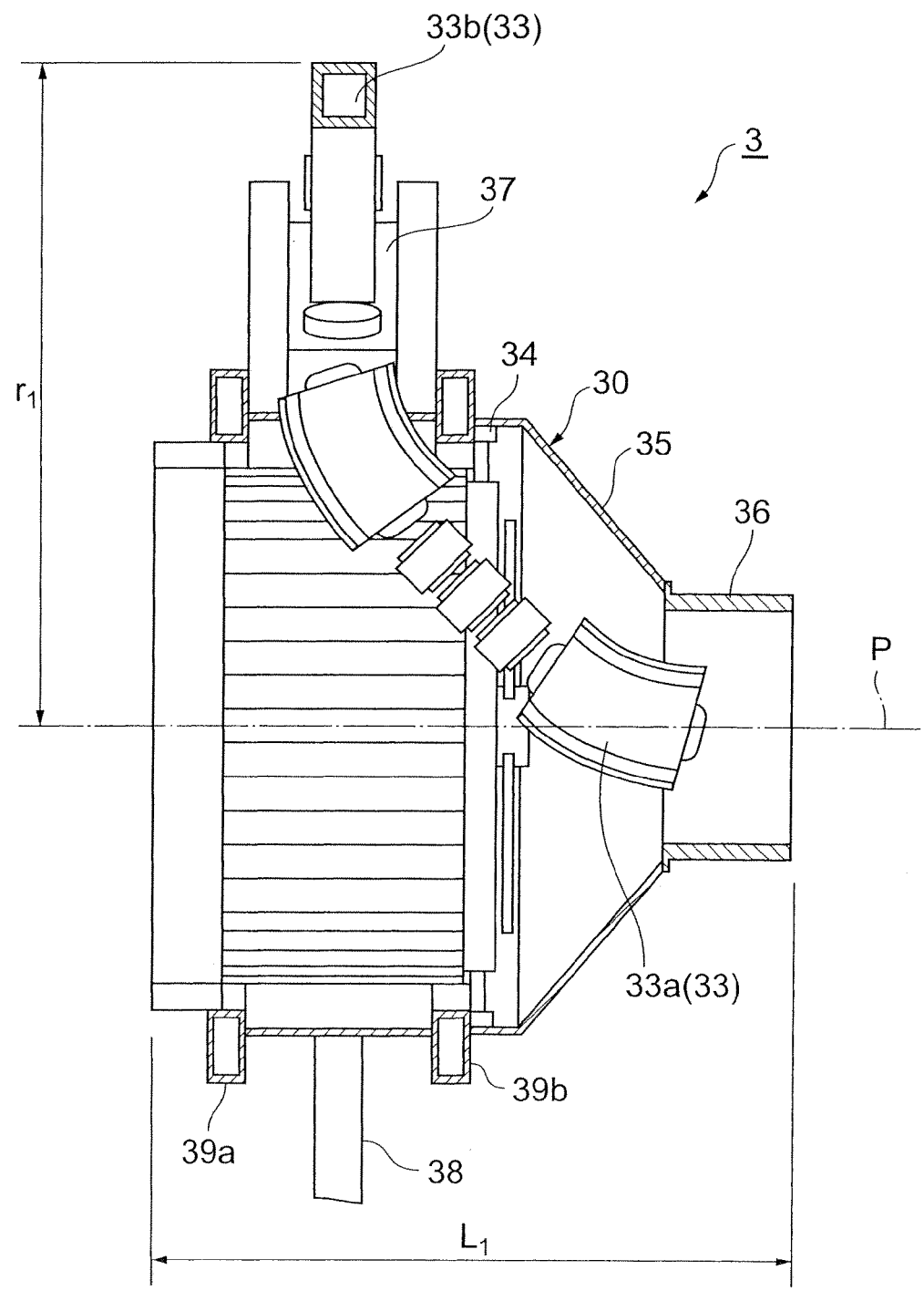
FIG. 4 is a schematic cross-sectional view of the rotating gantry according to this embodiment taken along the rotation axis.
Figure 5:
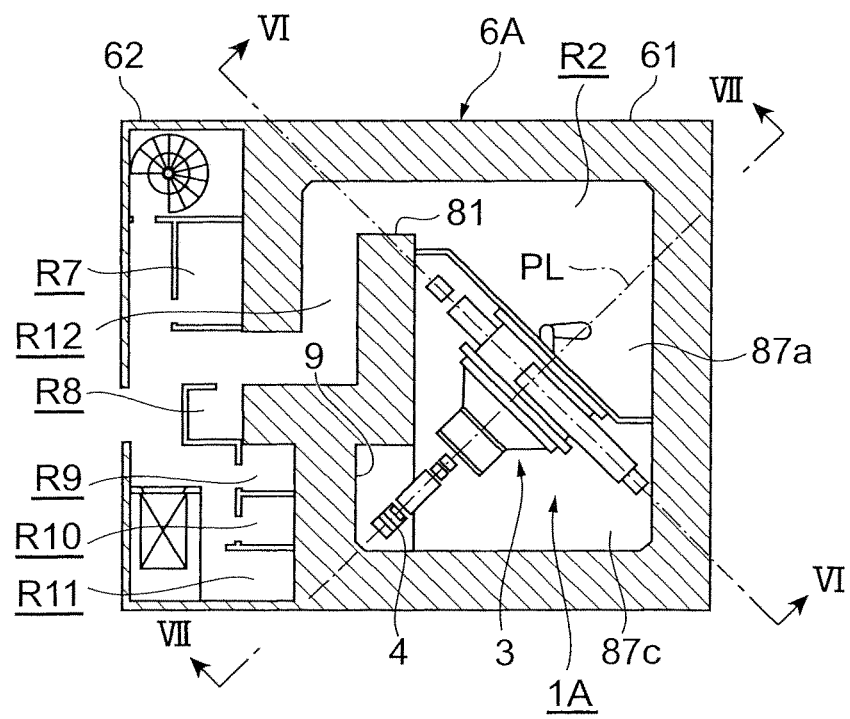
FIG. 5 is a view showing the disposition of the particle radiation therapy equipment on the first floor of a building.
Figure 6:
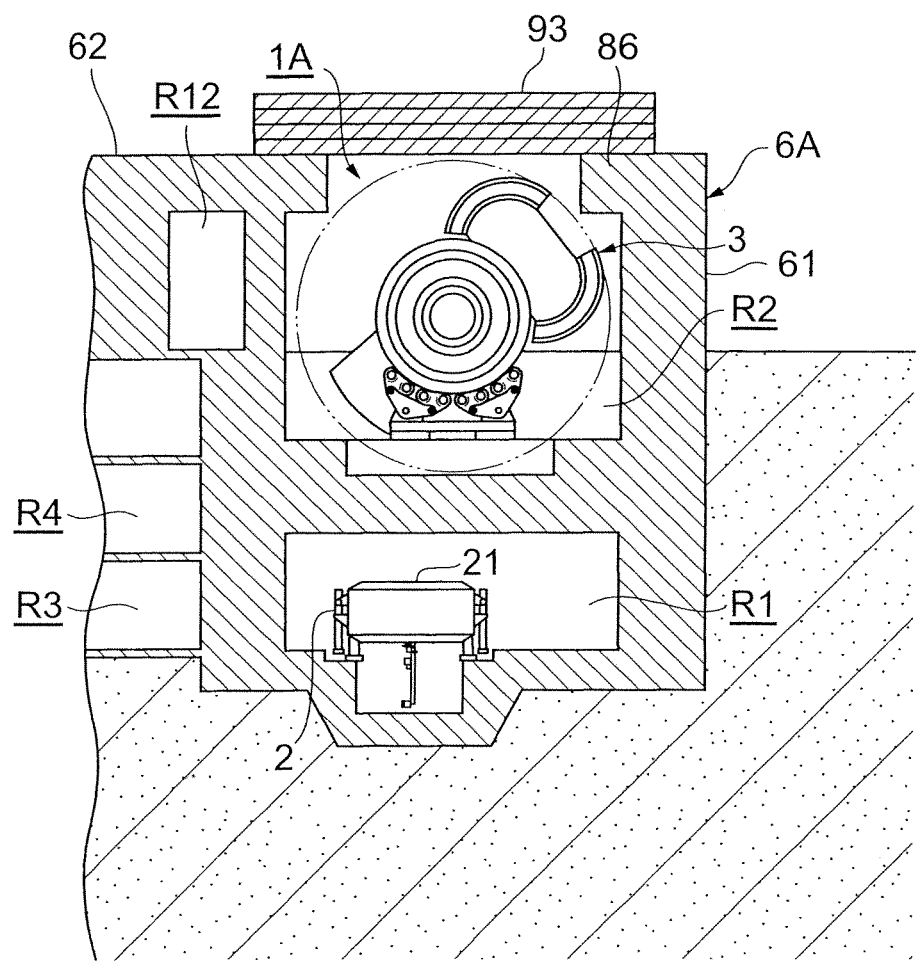
FIG. 6 is a schematic cross-sectional view of the building taken along a line VI-VI of FIG. 5.

As shown in FIGS. 2 to 4, the rotating gantry 3 includes a treatment table 31 (see FIG. 3) on which a patient lies; a rotating unit 30 that is provided so as to surround the treatment table 31; an irradiation unit 32 that is disposed in the rotating unit 30 and irradiates the patient, who lies on the treatment table 31, with a proton beam, and an introduction line 33 that introduces the proton beam guided by the guide line 5 to the irradiation unit 32. The rotating gantry 3 is rotationally driven by a motor (not shown) and the rotation of the rotating gantry is stopped by a brake device (not shown). Meanwhile, in the following description, the front face of the rotating gantry 3 means a side surface where the treatment table 31 is disposed and the rotating unit 30 is opened so as to allow a patient to enter or exit, and the rear face of the rotating gantry means the rear surface of the rotating gantry.

The rotating unit 30 is rotatable and is provided with a first cylindrical portion 34, a cone portion 35, and a second cylindrical portion 36 in this order from the front side. The first cylindrical portion 34, the cone portion 35, and the second cylindrical portion 36 are coaxially disposed and fixed to one another. The irradiation unit 32 is disposed on the inner surface of the first cylindrical portion 34, and faces the axis of the first cylindrical portion 34. The treatment table 31 is disposed near the axis (rotation axis) P of the first cylindrical portion 34. The diameter of the second cylindrical portion 36 is smaller than that of the first cylindrical portion 34, and the cone portion 35 is formed in a conical shape so as to connect the first cylindrical portion 34 to the second cylindrical portion 36.

A front ring 39a is disposed at the outer peripheral portion of the front end of the first cylindrical portion 34, and a rear ring 39b is disposed at the outer peripheral portion of the rear end of the first cylindrical portion 34. The first cylindrical portion 34 is rotatably supported by a roller device 40 (see FIG. 2) that is disposed below the first cylindrical portion 34. The outer peripheral surfaces of the front and rear rings 39a and 39b come into contact with the roller device 40, and torque is applied to the front and rear rings by the roller device 40.

The introduction line 33 is connected to the guide line 4 on the rear side of the rotating gantry 3. The introduction line 33 is provided with two sets of deflecting electromagnets corresponding to 45° and two sets of deflecting electromagnets corresponding to 135°. The introduction line 33 includes a radial introduction line 33a that communicates with the guide line 4 and extends in the radial direction, and a circumferential introduction line 33b that is connected to the rear end of the radial introduction line 33a and extends in the circumferential direction. Meanwhile, a beam transport pipe (not shown) is provided at the introduction line 33 along the track of the proton beam.

The radial introduction line 33a is a path portion which is curved at an angle of 90° (45°×2) with respect to the rotation axis P from the start end portion thereof communicating with the guide line 4 on the rotation axis P of the second cylindrical portion 36 and extends in the radial direction and of which the terminal end portion protrudes to the outside of the first cylindrical portion 34. Further, the circumferential introduction line 33b is a path portion which is curved and extends at an angle of 135° in the circumferential direction of the rotating unit 30 from the start end portion thereof communicating with the terminal end portion of the radial introduction line 33a and is curved toward the inside in the radial direction at an angle of 135° and of which the terminal end portion communicates with the irradiation unit 32.

The circumferential introduction line 33b is disposed in the circumferential direction at a position that is outwardly distant from the outer peripheral surface of the first cylindrical portion 34, and is supported by amount 37. The mount 37 is formed so as to protrude outward in the radial direction from the outer peripheral surface of the first cylindrical portion 34.

A counter weight 38 is provided so as to face the circumferential introduction line 33b and the mount 37 with the rotation axis P interposed therebetween. The counter weight 38 is fixed to the outer peripheral surface of the first cylindrical portion 34 and is provided so as to protrude outward in the radial direction. Since the counter weight 38 is provided, the weight balance between the counter weight and the mount 37 and the introduction line 33 is secured. Further, if the distance between the rotation axis P and the outer edge of the counter weight 38 is smaller than the distance between the rotation axis P and the outer edge of the introduction line 33, it is possible to reduce the size of the building 6A.

Moreover, the rotating gantry 3 of this embodiment is formed in a thin shape so that the length $L_1$ of the rotating gantry of this embodiment in a longitudinal direction along the rotation axis P is smaller than the maximum outer diameter (maximum width) of the rotating unit 30. The length $L_1$ of the rotating gantry in the longitudinal direction is, for example, the distance $L_1$ between the front end of the first cylindrical portion 34 and the rear end of the second cylindrical portion 36. The maximum outer diameter of the rotating unit 30 is the maximum outer diameter of the rotating unit in a direction orthogonal to the rotation axis P, and corresponds to a portion corresponding to the distance $r_1$ between the rotation axis P and the outer edge of the circumferential introduction line 33b (maximum outer diameter=radius $r_1 \times 2$). Meanwhile, a portion corresponding to the distance between the rotation axis P and the outer edge of the counter weight 38 may have the maximum outer diameter.

The guide line 4 (see FIGS. 1 and 7) includes a beam transport pipe (not shown) through which a proton beam passes, a plurality of quadrupole electromagnets 41 that adjusts the shape of the proton beam by converging the proton beam, a plurality of deflecting electromagnets 42 that is disposed to form the curved track of the proton beam, and the like.

The building 6A and the disposition of the respective devices of the particle radiation therapy equipment 1A in the building 6A will be described below with reference to FIG. 1 and FIGS. 5 to 8. The building 6A is a building having, for example, a reinforced concrete structure or a steel skeleton concrete structure, and the respective chambers of the building are separated from each other by radiation shield walls made of concrete. Further, the building 6A includes a main building portion (building) 61 and a sub-building portion 62. The cyclotron 2, the rotating gantry 3, and the guide line 4, which form the main components of the particle radiation therapy equipment 1A, are installed in the main building portion. Respective chambers in which other items of equipment such as power-supply equipment are disposed, a chamber where a patient is received, and the like are formed at the sub-building portion 62. The sub-building portion 62 has a multi-story structure with three stories below and one story above the ground. A cooling device chamber R3 is formed in the third basement, and a power source chamber R4 and the like is formed in the second basement. Furthermore, a radioactive material chamber R5, a staff room R6, and the like are formed in the first basement. A treatment control room R7, a front desk R8, a locker room R9, a toilet R10, a patient waiting room R11, a passage R12 for allowing a patient to enter the gantry chamber R2, and the like are formed on the first floor.

The main building portion 61 has a multi-story structure with one story below and one story above the ground. The cyclotron 2 is installed in a cyclotron chamber (accelerator chamber) R1 that is formed in the first basement (bottom floor), and the rotating gantry 3 is installed in the gantry chamber (irradiation device chamber) R2 that is formed immediately above the cyclotron chamber R1 on the first floor. Moreover, a communication passage 9, in which the guide line 4 for allowing the cyclotron 2 and the rotating gantry 3 to communicate with each other is disposed, is formed at the main building portion 61.

Figure 8:
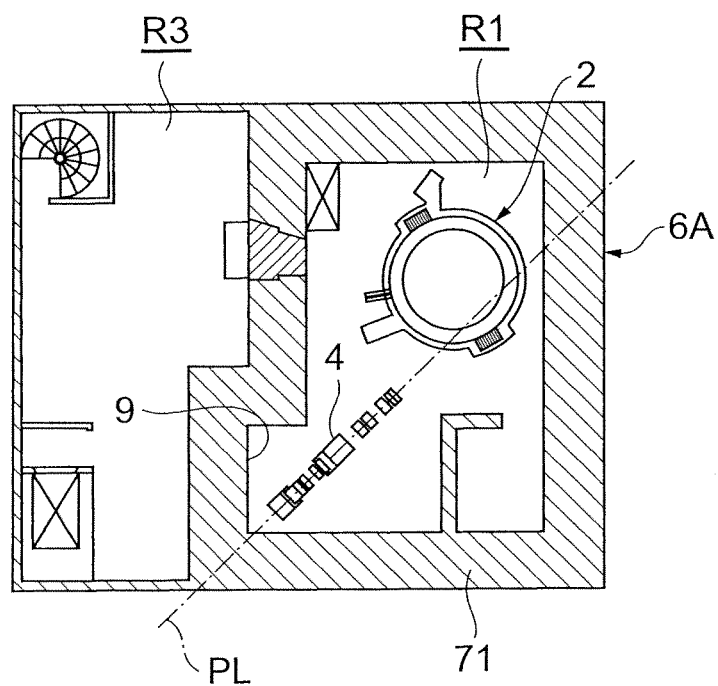
FIG. 8 is a view showing the disposition of the particle radiation therapy equipment in the first basement of a building.

The cyclotron chamber R1 is formed in a substantially rectangular shape in plan view, and is surrounded by a (radiation) shield wall 71 (see FIG. 8). The cyclotron 2 is disposed on the front side of the cyclotron chamber R1 (the upper side in FIG. 8), and a proton beam generated by the cyclotron 2 is directed from the rear side of the cyclotron 2. Further, the communication passage 9 formed in the vertical direction is connected to the rear side of the cyclotron chamber R1. The communication passage 9 extends in the up-down direction (vertical direction), and communicates with the rear side of the gantry chamber R2 (the lower side in FIG. 5).

The guide line 4 (see FIG. 7) communicates with the vacuum box 21 of the cyclotron 2, extends in the horizontal direction, is curved upward in the vertical direction at an angle of about 90°, passes through the communication passage 9, is curved again in the horizontal direction at an angle of about 90°, and communicates with the rotating gantry 3. The plurality of quadrupole electromagnets 41 is disposed at linear portions of the guide line 4 and two sets of deflecting electromagnets 42, which each change the path by a rotation angle of 45°, are disposed at curved portions, so that a curve of a total angle of about 90° in total is formed. Further, the guide line 4 is disposed on a virtual plane PL that extends two-dimensionally, that is, in the up-down direction (vertical direction). As a result, it may be possible to reduce the number of quadrupole electromagnets 41 and the deflecting electromagnets 42 that converge and curve the proton beam guided by the guide line 4.

The gantry chamber R2 is formed immediately above the cyclotron chamber R1. The gantry chamber R2 is formed in a substantially rectangular shape in plan view, and is partitioned by a radiation shield wall 81. An entrance floor portion 87a through which a patient enters or exits, and a lower floor portion 87c that is lower than the entrance floor portion 87a are formed at the gantry chamber R2. The rotating gantry 3 is installed at the lower floor portion 87c so that the treatment table 31 faces the entrance floor portion 87a. Accordingly, the rotating gantry is formed so that a patient can easily reach the treatment table 31. Moreover, an entrance, which communicates with the labyrinthine passage R12, is formed at the wall of the gantry chamber R2 corresponding to the entrance floor portion 87a.

The portion of the rotating gantry 3 having the maximum width is disposed along the maximum width of an installation space of the rotating gantry 3 in the gantry chamber R2. Specifically, the rotating gantry 3 is disposed along the diagonal line of the gantry chamber R2 that is formed in a substantially rectangular shape, so that an innovation or efficiently using an inner space of the gantry chamber R2 is made.

As shown in FIGS. 1, 2, 6, and 7, an opening 92 which avoids interference with the rotating unit 30 of the rotating gantry 3 and through which components are carried is formed at a ceiling 86 of the main building portion 61. The opening 92 is covered with a shield member 93, which is made of a separate material which is different from the material of the ceiling 86, from the outside of the gantry chamber R2 (the main building portion 61). The shield member 93 may be formed by stacking a plurality of shield plates 93a made of, for example, lead. Meanwhile, shield plates made of concrete, which is the same material as the material of the ceiling 86, may be stacked as the shield member 93. Furthermore, for example, a block body, which does not have the shape of a plate, may be used as the shield member.

Moreover, the shield member 93 may be made of heavy concrete as a separate material. The shield member 93 made of heavy concrete is more expensive than the shield member 93 made of general concrete, but has high radiation shielding properties. For example, when a shield member made of heavy concrete is used, the thickness of the shield member may be about ⅔ of the thickness of a shield member made of general concrete. Further, if the shield member 93 which is modularized as a plate-like component is used, it may be possible to easily perform construction.

In the particle radiation therapy equipment 1A according to this embodiment, the cyclotron 2 and the rotating gantry 3 are installed on different floors of the building 6A, respectively, and the rotating gantry 3 is particularly installed immediately above the cyclotron 2. Accordingly, it may be possible to reduce as far as possible the installation area occupied by the equipment. As a result, it is easy to efficiently install the cyclotron 2 and the rotating gantry 3 at a predetermined site.

Meanwhile, one rotating gantry 3 has been installed on the first floor in this embodiment. Even when the number of rotating gantries is increased, the cyclotron 2 is installed on the bottom floor of the building 6A. Accordingly, many cyclotrons 2 do not need to be moved, two floors or three floors are formed above the first floor on which the rotating gantry 3 is already installed, and rotating gantries 3 may be appropriately installed on these upper floors. Therefore, it is easy to increase the number of rotating gantries 3. Meanwhile, in anticipation of an increase in future numbers of rotating gantries, for example, the cyclotron chamber R1 is formed in the third basement, the gantry chamber R2 is formed in the second basement, and the first basement is made empty. Accordingly, if a new gantry chamber R2 is formed in the first basement and a rotating gantry 3 is installed in the new gantry chamber when the number of rotating gantries is to be increased, the operating burden for carrying and installing the rotating gantry 3, which is a heavy object, are reduced.

Further, the irradiation device of this embodiment is the rotating gantry 3 that includes the rotating unit 30 and the irradiation unit 32. The rotating unit is rotatable about the rotation axis P. The irradiation unit can irradiate an irradiation target with a proton beam generated by the cyclotron 2, and the irradiation direction of the irradiation unit is changed as the rotating unit 30 is rotated. Furthermore, since the rotating gantry 3 is formed in a thin shape so that the length of the rotating gantry in the direction of the rotation axis P is smaller than the maximum outer diameter (maximum width) of the rotating gantry in a direction orthogonal to the rotation axis P, the rotating gantry is effective in allowing the reduction of the size of the facility. Therefore, it is easy to efficiently install the cyclotron 2 and the rotating gantry 3 at a predetermined site.

(Second Embodiment)

Figure 9:
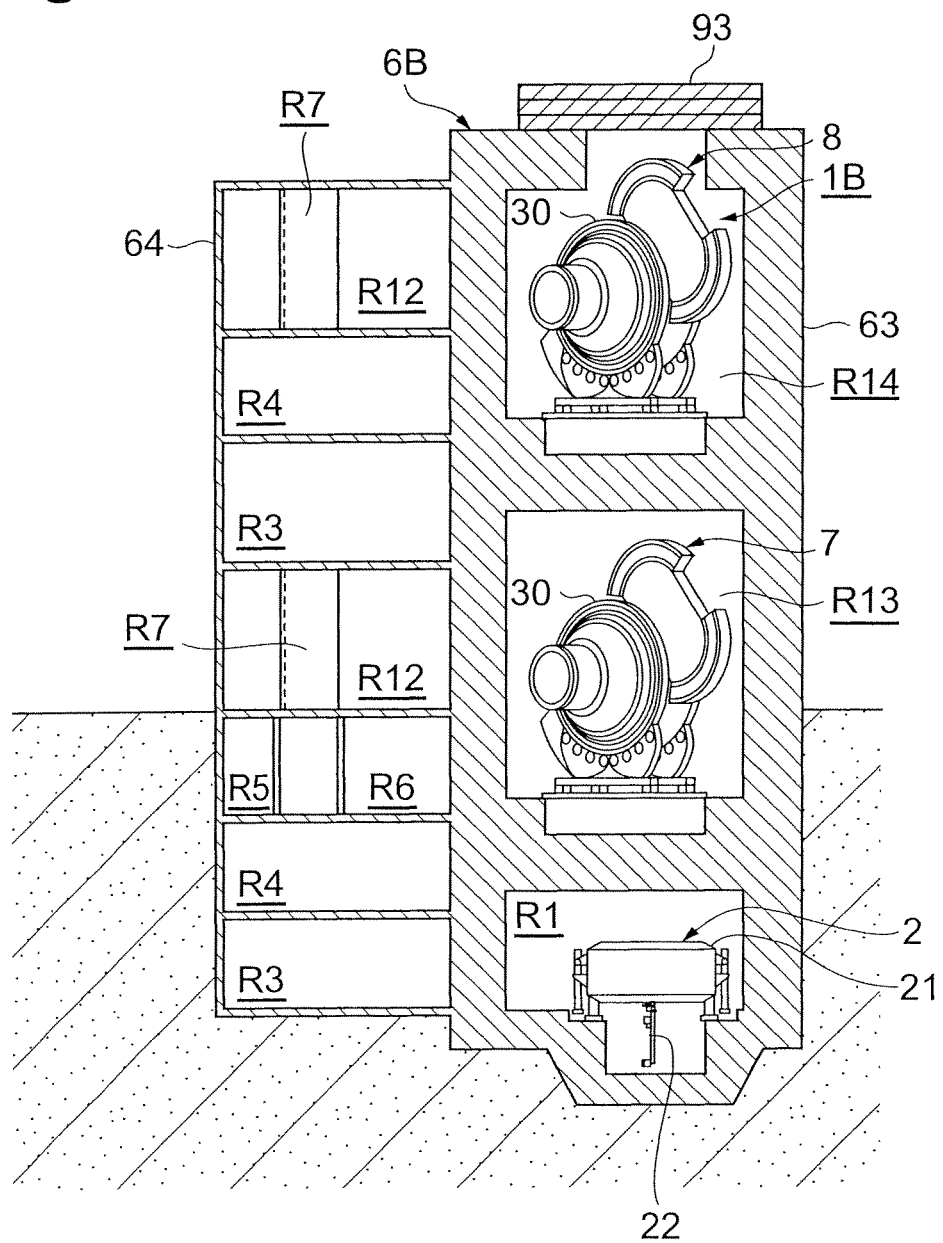
FIG. 9 is a side cross-sectional view of particle radiation therapy equipment according to a second embodiment of the invention.
Figure 10:
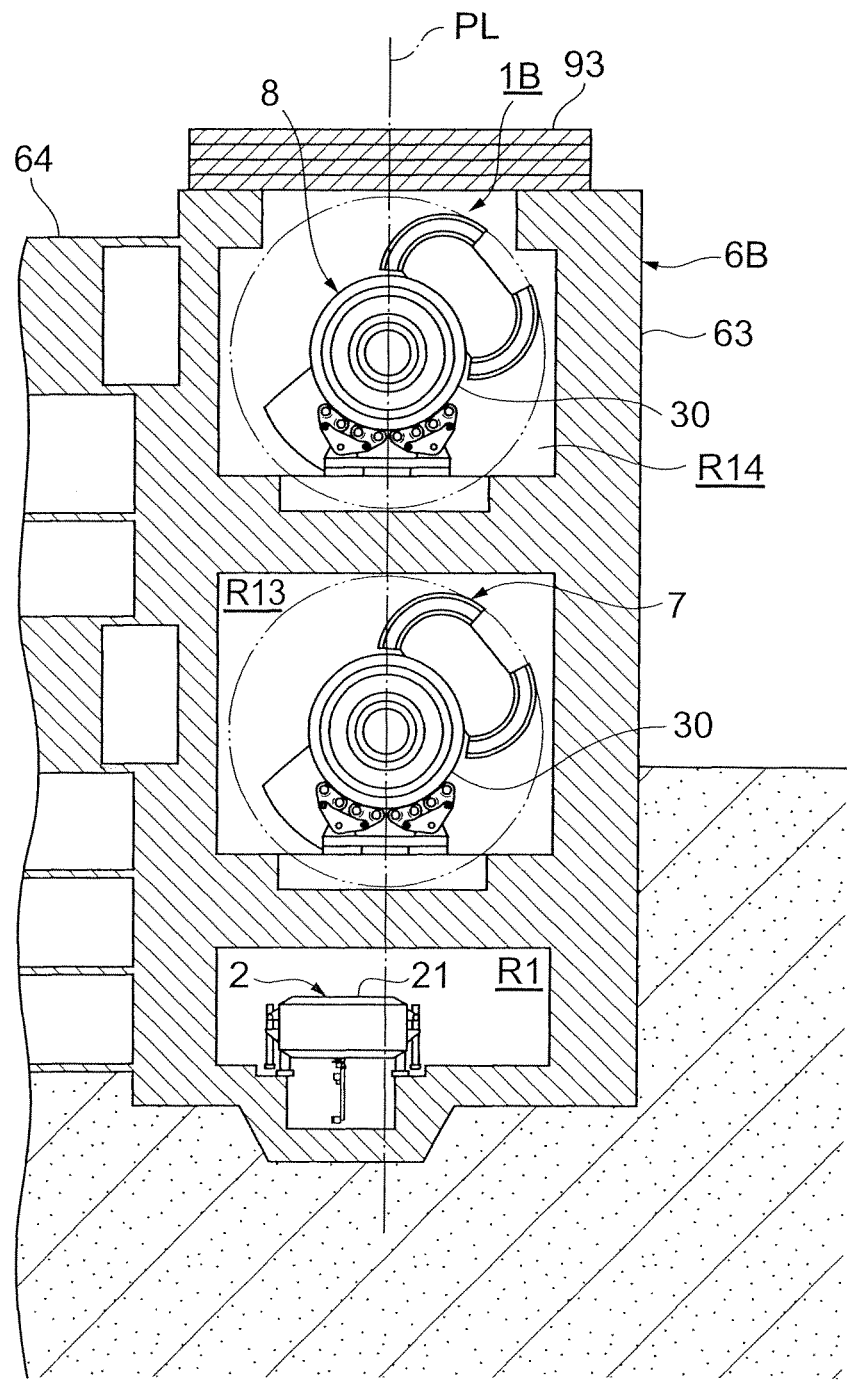
FIG. 10 is a side cross-sectional view of the particle radiation therapy equipment according to the second embodiment as seen from a direction parallel to the rotation axis of a rotating gantry.
Figure 11:
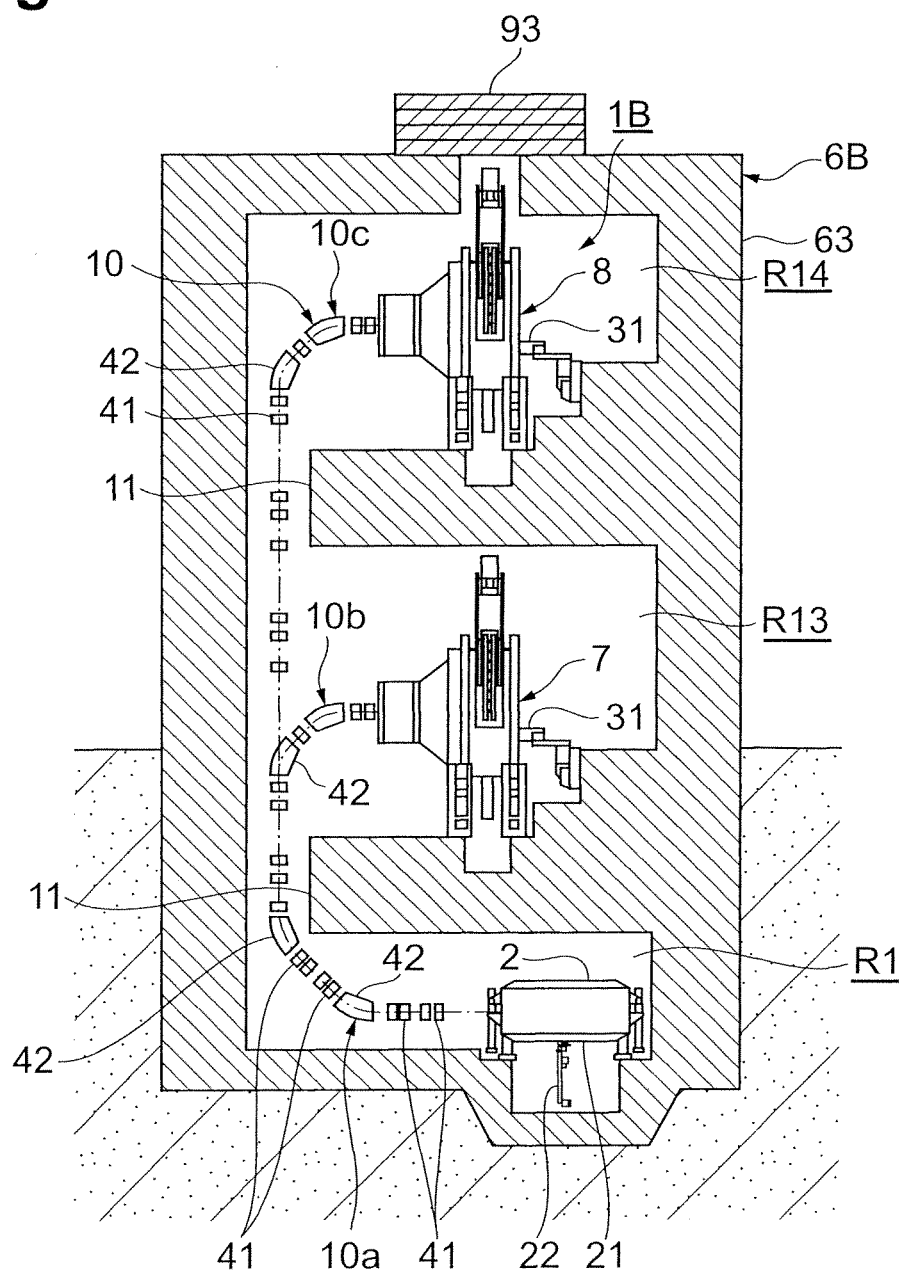
FIG. 11 is a side cross-sectional view of the particle radiation therapy equipment according to the second embodiment as seen from a direction orthogonal to the rotation axis of the rotating gantry.

Next, particle radiation therapy equipment (accelerated particle irradiation equipment) 1B according to a second embodiment of the invention will be described with reference to FIGS. 9 to 11. Meanwhile, similar elements and members of the particle radiation therapy equipment 1B according to this embodiment to those of the particle radiation therapy equipment 1A according to the first embodiment are denoted by the same reference numerals, and a detailed description thereof will be omitted.

A building 6B of this embodiment is a building having, for example, a reinforced concrete structure or a steel skeleton concrete structure, and the respective chambers of the building are separated from each other by radiation shield walls made of concrete. Further, the building 6B includes a main building portion (building) 63 and a sub-building portion 64. The sub-building portion 64 has a multi-story structure with three stories below and four stories above the ground. Cooling device chambers R3, power source chambers R4, a staff room R6, a radioactive material storage chamber R5, treatment control rooms R7, and the like are formed on the respective floors.

The main building portion 63 has a multi-story structure with one story below and two stories above the ground. A cyclotron (particle accelerator) 2 is installed in a cyclotron chamber (accelerator chamber) R1 that is formed in the first basement (bottom floor), a first rotating gantry 7 is installed in a first gantry chamber R13 that is formed immediately above the cyclotron chamber R1 on the first floor, and a second rotating gantry 8 is installed in a second gantry chamber R14 that is formed immediately above the first gantry chamber R13 on the second floor. Moreover, a communication passage 11, in which a guide line 10 for allowing the cyclotron 2, the first rotating gantry 7, and the second rotating gantry 8 to communicate with each other is disposed, is formed at the main building portion 63. Meanwhile, since the first and second rotating gantries 7 and 8 have substantially the same structure as that of the rotating gantry 3 of the first embodiment, a detailed description thereof will be omitted.

The guide line 10 includes a take-off path 10*a*, a first branched path 10*b*, and a second branched path 10*c*. The take-off path 10*a* communicates with a vacuum box 21 of the cyclotron 2, extends in the horizontal direction, is curved upward in the vertical direction at an angle of about 90°, and passes through the communication passage 11. The first branched path 10*b* is branched from the take-off path 10*a*, is curved in the horizontal direction at an angle of about 90° with respect to the take-off path 10*a*, and communicates with the first rotating gantry 7. The second branched path 10*c* is branched from the take-off path 10*a*, is curved in the horizontal direction at an angle of about 90° with respect to the take-off path 10*a*, and communicates with the second rotating gantry 8.

A plurality of quadrupole electromagnets 41 is disposed at linear portions of the guide line 10 and two sets of deflecting electromagnets 42, which each change the path by a rotation angle of 45°, are disposed at curved portions, so that a curve of a total angle of about 90° in total is formed. Further, the take-off path 10*a*, the first branched path 10*b*, and the second branched path 10*c* of the guide line 10 are disposed on a virtual plane PL (see FIG. 10) that extends two-dimensionally, that is, in the up-down direction (vertical direction). As a result, it may be possible to reduce the number of the quadrupole electromagnets 41 and the deflecting electromagnets 42 that converge and curve the proton beam guided by the guide line 10.

Here, if the track of a proton beam is disposed two-dimensionally on the same virtual plane PL, it is easy to maintain the symmetry of the track of a proton beam. However, if the track of a proton beam is deviated three-dimensionally, it is difficult to perform the adjustment for maintaining the symmetry of the track of a proton beam. Since the plurality of branched paths 10*b* and 10*c* and the take-off path 10*a* of the guide line 10 are disposed on the same virtual plane PL in the particle radiation therapy equipment 1B according to this embodiment, it is easy to maintain the symmetry of the track of a proton beam and the particle radiation therapy equipment is effective in improving the accuracy of irradiation.

According to the particle radiation therapy equipment 1B of this embodiment, it is easy to efficiently install the cyclotron 2, the first rotating gantry 7, and the second rotating gantry 8 at a predetermined site like the particle radiation therapy equipment 1A of the first embodiment. Further, since the cyclotron 2 is installed on the bottom floor of the building 6B, it is easy to increase the number of rotating gantries 7 and 8.

Furthermore, the particle radiation therapy equipment 1B includes the plurality of rotating gantries 7 and 8, and the plurality of rotating gantries 7 and 8 is installed on different floors of the main building portion 63, respectively. Accordingly, since it may be possible to install the plurality of rotating gantries 7 and 8 so that the rotating gantries are arranged in line in the up-down direction in accordance with the site area, it is easy to efficiently install the plurality of rotating gantries 7 and 8 at a predetermined site.

(Third Embodiment)

Figure 12:
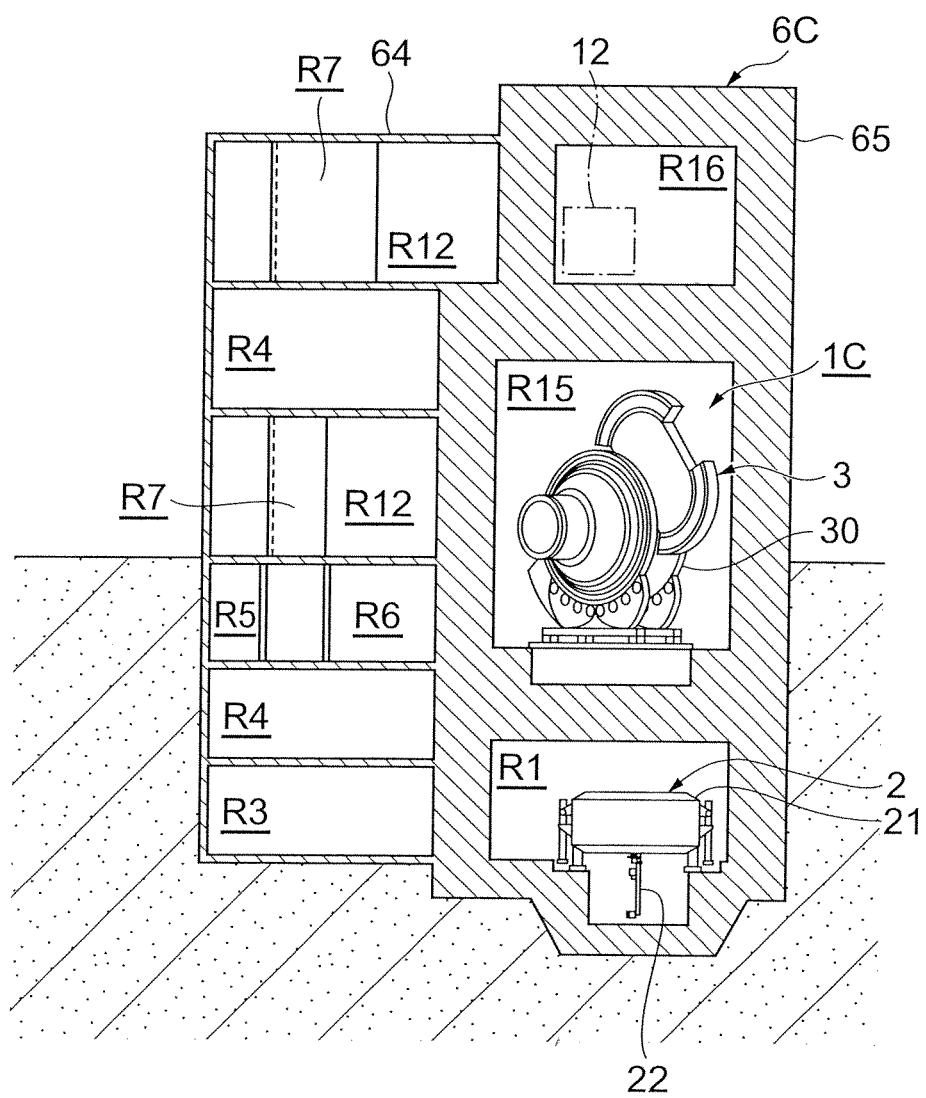
FIG. 12 is a side cross-sectional view of particle radiation therapy equipment according to a third embodiment of the invention.
Figure 13:
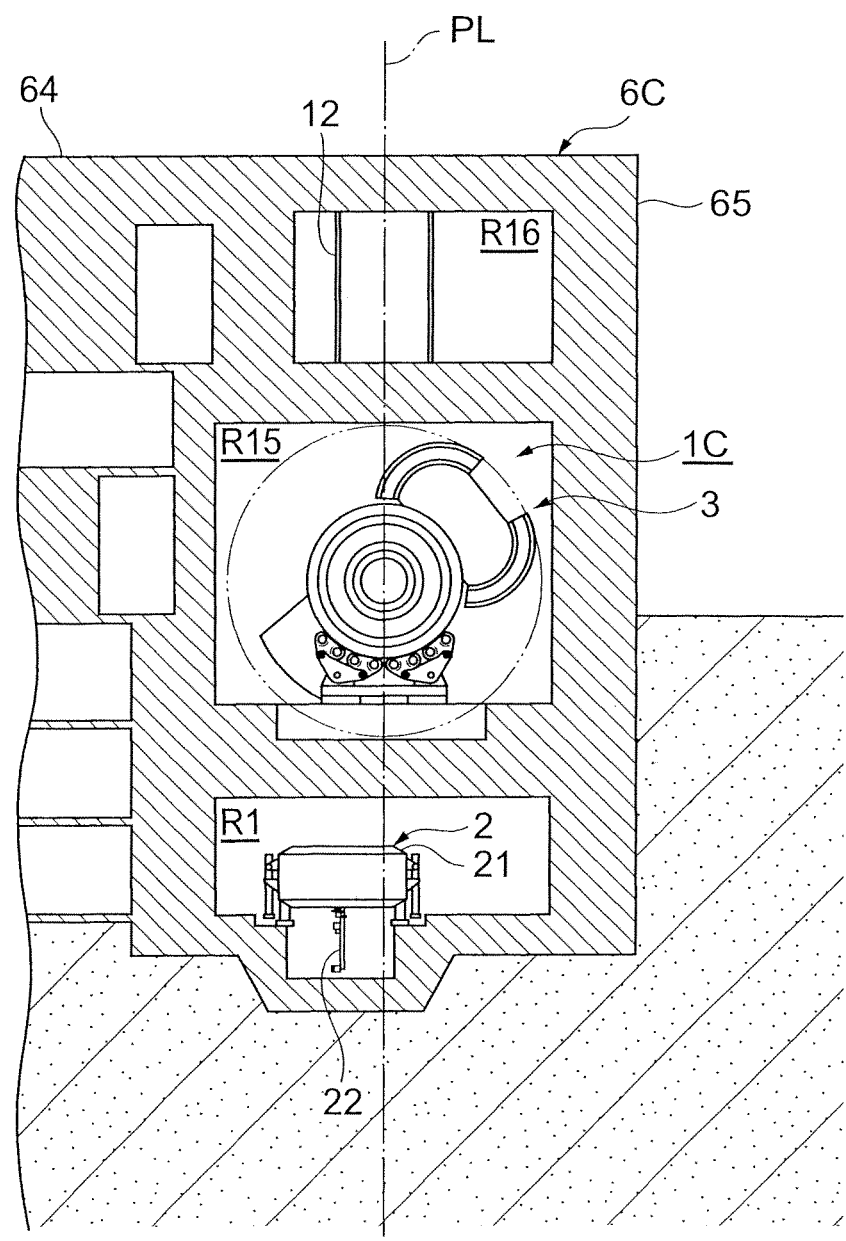
FIG. 13 is a side cross-sectional view of the particle radiation therapy equipment according to the third embodiment as seen from a direction parallel to the rotation axis of the rotating gantry.
Figure 14:
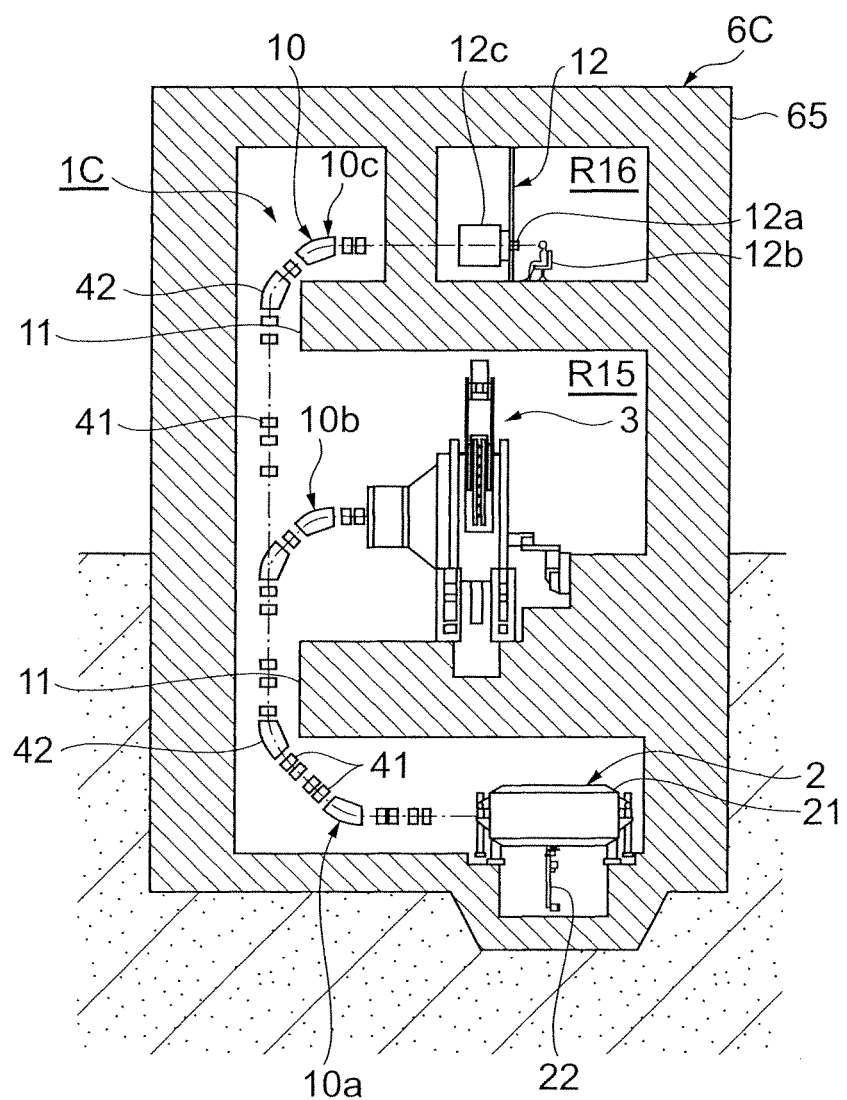
FIG. 14 is a side cross-sectional view of the particle radiation therapy equipment according to the third embodiment as seen from a direction orthogonal to the rotation axis of the rotating gantry.

Next, particle radiation therapy equipment (accelerated particle irradiation equipment) 1C according to a third embodiment of the invention will be described with reference to FIGS. 12 to 14. Meanwhile, similar elements and members of the particle radiation therapy equipment 1C according to this embodiment to those of the particle radiation therapy equipment 1A according to the first embodiment or the particle radiation therapy equipment 1B according to the second embodiment are denoted by the same reference numerals, and a detailed description thereof will be omitted.

A building 6C of this embodiment is a building having, for example, a reinforced concrete structure or a steel skeleton concrete structure, and the respective chambers of the building are separated from each other by radiation shield walls made of concrete. Further, the building 6C includes a main building portion 65 and a sub-building portion 64.

The main building portion 65 has a multi-story structure with one story below and two stories above the ground. A cyclotron (particle accelerator) 2 is installed in a cyclotron chamber (accelerator chamber) R1 that is formed in the first basement (bottom floor), a rotating gantry 3 is installed in a gantry chamber R15 that is formed immediately above the cyclotron chamber R1 on the first floor, and a stationary irradiation device 12 is installed in a stationary irradiation chamber R16 that is formed immediately above the gantry chamber R15 on the second floor. Moreover, a communication passage 11, in which a guide line 10 for allowing the cyclotron 2, the rotating gantry 3, and the stationary irradiation device 12 to communicate with each other is disposed, is formed at the main building portion 65.

The stationary irradiation device 12 includes a treatment table 12*b* on which a patient sits; an irradiation unit 12*a* that irradiates the patient, who sits on the treatment table 12*b*, with a proton beam; and an introduction line 12*c* that introduces the proton beam guided by the guide line 10 to the irradiation unit 12*a*. The stationary irradiation device 12 does not include a rotating unit 30 unlike the above-mentioned rotating gantry 3. The irradiation unit 12*a* is fixed at a predetermined position, and the irradiation of a specific portion of a patient with a proton beam is adjusted by up-down movement or rotation of the treatment table 12*b*. The stationary irradiation device 12 is used for the treatment of diseases of the prostate gland or the eyes.

In the particle radiation therapy equipment 1C according to this embodiment, the cyclotron 2, the rotating gantry 3, and the stationary irradiation device 12 are installed on different floors of the building 6C, respectively, and the rotating gantry 3 or the stationary irradiation device 12 is particularly installed immediately above or above the cyclotron 2. Accordingly, it may be possible to reduce as far as possible the installation area occupied by the equipment. As a result, it is easy to efficiently install the cyclotron 2, the rotating gantry 3, and the stationary irradiation device 12 at a predetermined site. Further, since the cyclotron 2 is installed on the bottom floor of the building 6C, it is easy to increase the number of rotating gantries 3.

Furthermore, the take-off path 10a, the first branched path 10b, and the second branched path 10c of the guide line 10 are disposed on a virtual plane PL that extends two-dimensionally, that is, in the up-down direction (vertical direction). As a result, it may be possible to reduce the numbers of quadrupole electromagnets 41 and deflecting electromagnets 42 that converge and curve the proton beam guided by the guide line 10. In addition, since the take-off path 10a and the plurality of branched paths 10b and 10c are disposed on the same virtual plane PL, it is easy to maintain the symmetry of the track of a proton beam and the particle radiation therapy equipment is effective in improving the accuracy of irradiation.

Further, the particle radiation therapy equipment 1C includes two kinds of irradiation devices, that is, the rotating gantry 3 and the stationary irradiation device 12, and the rotating gantry 3 and the stationary irradiation device 12 are installed on different floors of the main building portion 65, respectively. Accordingly, since it may be possible to install the rotating gantry 3 and the stationary irradiation device 12 so that the rotating gantry and the stationary irradiation device are arranged in line in the up-down direction in accordance with the site area, it is easy to efficiently install different kinds of the rotating gantry 3 and the stationary irradiation device 12 at a predetermined site.

Furthermore, the particle radiation therapy equipment 1C includes the rotating gantry 3 that is a rotary irradiation device and the stationary irradiation device 12 that includes the irradiation unit 12a for which the irradiation direction is fixed. Accordingly, it is possible to separately use the rotating gantry 3 and the stationary irradiation device 12. Therefore, the particle radiation therapy equipment is effective for appropriately irradiating a patient with a proton beam.

(Fourth Embodiment)

Figure 15:
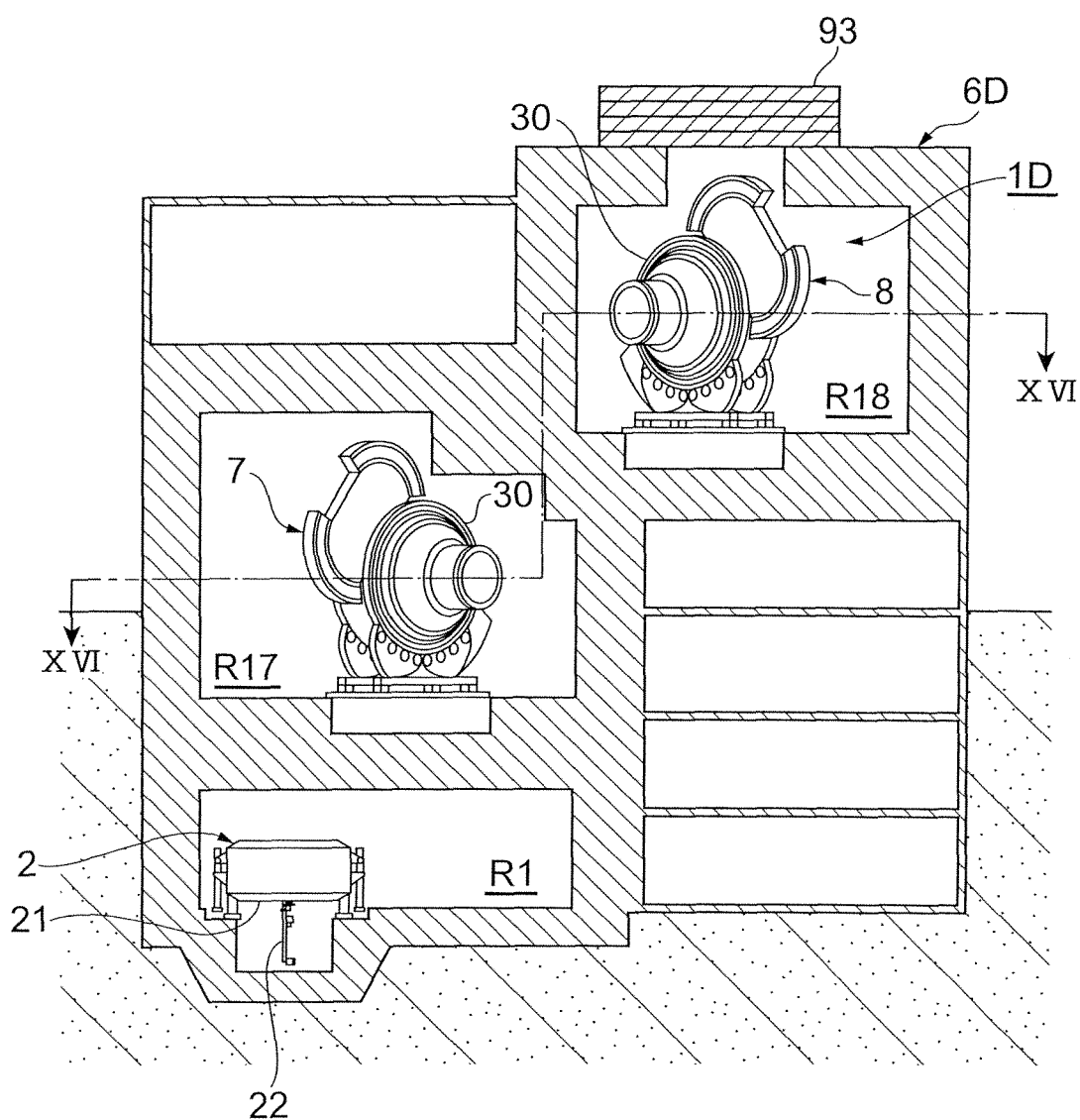
FIG. 15 is a side cross-sectional view of particle radiation therapy equipment according to a fourth embodiment of the invention.
Figure 16:
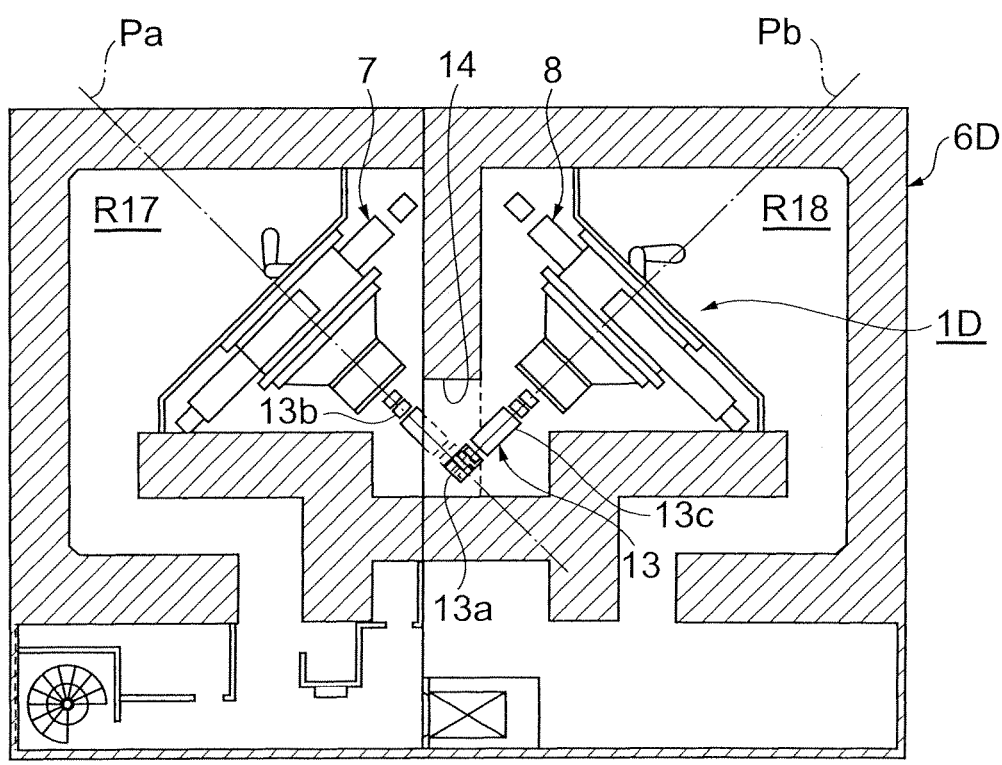
FIG. 16 is a cross-sectional view of a building taken along a line XVI-XVI of FIG. 15.

Next, particle radiation therapy equipment (accelerated particle irradiation equipment) 1D according to a fourth embodiment of the invention will be described with reference to FIGS. 15 and 16. Meanwhile, similar elements and members of the particle radiation therapy equipment 1D according to this embodiment to those of the pieces of particle radiation therapy equipment 1A to 1C according to the first to third embodiments are denoted by the same reference numerals, and a detailed description thereof will be omitted.

A building 6D of this embodiment is a building having, for example, a reinforced concrete structure or a steel skeleton concrete structure, and the respective chambers of the building are separated from each other by radiation shield walls made of concrete. Further, the main structure of the building 6D is a multi-story structure with one story below and two stories above the ground. A cyclotron (particle accelerator) 2 is installed in a cyclotron chamber (accelerator chamber) R1 that is formed in the first basement (bottom floor). Furthermore, a first gantry chamber R17 is formed immediately above the cyclotron chamber R1 on the first floor, and a first rotating gantry 7 is installed in the first gantry chamber R17. Moreover, a second gantry chamber R18 is formed on the second floor at a position that is deviated in the horizontal direction from a position immediately above the first gantry chamber R17, and a second rotating gantry 8 is installed in the second gantry chamber R18.

Further, a communication passage 14, in which a guide line 13 for allowing the cyclotron 2, the first rotating gantry 7, and the second rotating gantry 8 to communicate with each other is disposed, is formed at the building 6D. The communication passage (see FIG. 16) 14 is formed substantially at the center of the building 6D. The guide line 13 includes a take-off path 13a, a first branched path 13b, and a second branched path 13c. The take-off path 13a communicates with a vacuum box 21 of the cyclotron 2, extends in the horizontal direction, is curved upward in the vertical direction at an angle of about 90°, and passes through the communication passage 14. The first branched path 13b is branched from the take-off path 13a, is curved in the horizontal direction at an angle of about 90° with respect to the take-off path 13a, and communicates with the first rotating gantry 7. The second branched path 13c is branched from the take-off path 13a, is curved in the horizontal direction at an angle of about 90° with respect to the take-off path 13a, and communicates with the second rotating gantry 8. In the particle radiation therapy equipment 1D according to this embodiment, a virtual vertical plane Pa passing through the rotation axis P of the first rotating gantry 7 is not the same as a virtual vertical plane Pb passing through the rotation axis P of the second rotating gantry. Accordingly, the first and second branched paths 13b and 13c are not disposed on the same virtual plane.

In the particle radiation therapy equipment 1D, the cyclotron 2, the first rotating gantry 7, and the second rotating gantry 8 are installed on different floors of the building 6D, respectively. Accordingly, it may be possible to reduce as far as possible the installation area occupied by the equipment. As a result, it is easy to efficiently install the cyclotron 2 and the rotating gantries 7 and 8 at a predetermined site. Further, since the cyclotron 2 is installed on the bottom floor of the building 6D, it is easy to increase the number of rotating gantries 7 and 8.

Furthermore, since the first and second rotating gantries 7 and 8 are deviated in the horizontal direction and installed in a zigzag shape in the particle radiation therapy equipment 1D, it may be possible to install the second rotating gantry 8 while avoiding the highest portion of the first rotating gantry 7. Accordingly, it is easy to reduce the height of the building 6D.

Meanwhile, the first rotating gantry 7 has been disposed immediately above the cyclotron 2 in the particle radiation therapy equipment 1D. However, the first rotating gantry 7 may be disposed so as to be deviated in the horizontal direction from a position immediately above the cyclotron 2, and the second rotating gantry 8 may be disposed in a zigzag shape so as to be disposed above the cyclotron 2 in the vertical direction. Further, the rotating gantries 7 and 8, which are provided on both sides of a vertical line passing though the center of the cyclotron 2, may be disposed in a zigzag shape so as to be alternately deviated to the left and right sides.

(Fifth Embodiment)

Figure 17:
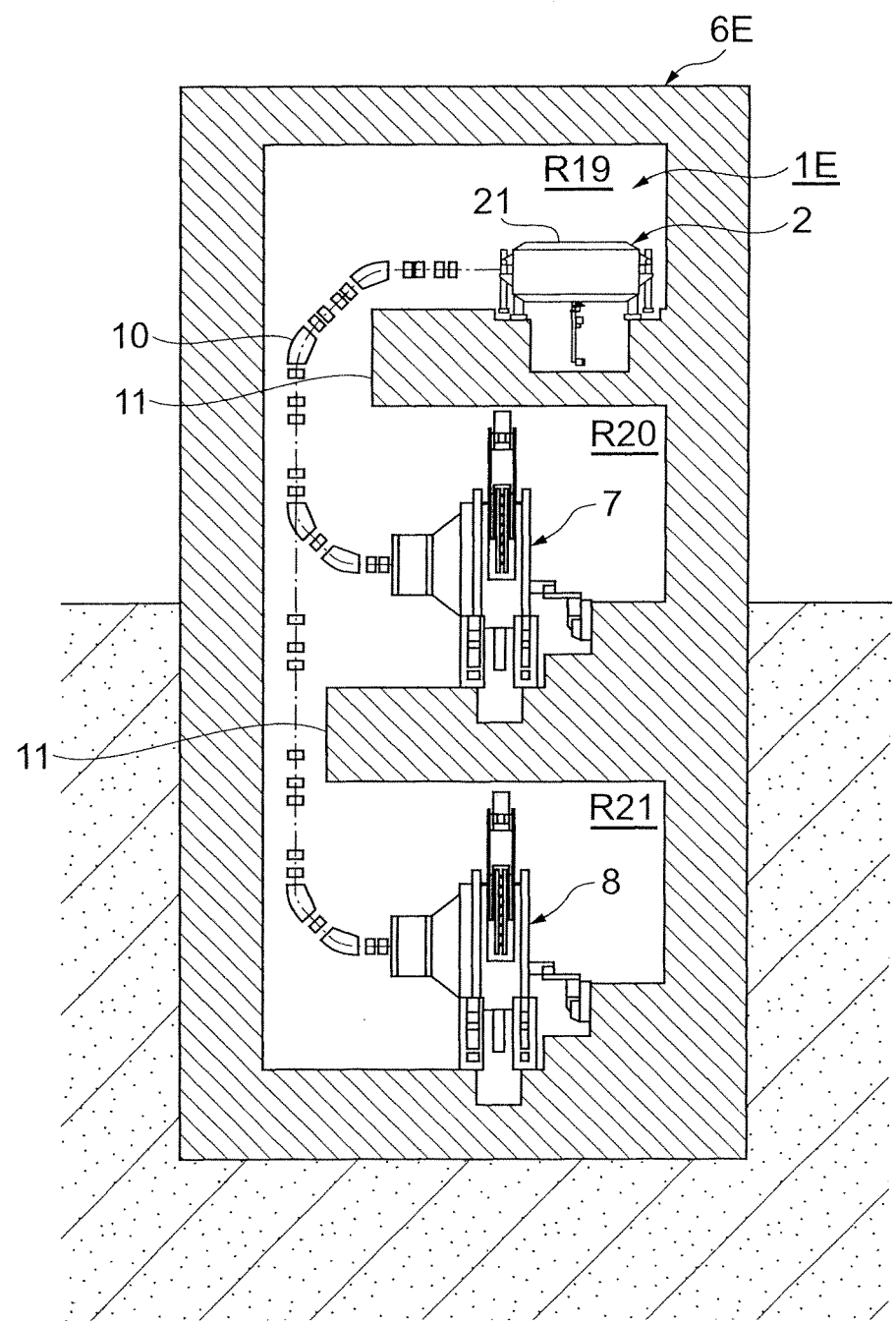
FIG. 17 is a side cross-sectional view of particle radiation therapy equipment according to a fifth embodiment of the invention.

Next, particle radiation therapy equipment (accelerated particle irradiation equipment) 1E according to a fifth embodiment of the invention will be described with reference to FIG. 17. Meanwhile, similar elements and members of the particle radiation therapy equipment 1E according to this embodiment to those of the pieces of particle radiation therapy equipment 1A to 1D according to the first to fourth embodiments are denoted by the same reference numerals, and a detailed description thereof will be omitted.

A building 6E of this embodiment is a building having, for example, a reinforced concrete structure or a steel skeleton concrete structure, and the respective chambers of the building are separated from each other by radiation shield walls made of concrete. Further, the building 6E has a multi-story structure with one story below and two stories above the ground. In the particle radiation therapy equipment 1E according to this embodiment, a first rotating gantry 7, a second rotating gantry 8, and a cyclotron 2 are reversely disposed in the vertical direction as compared to the above-mentioned respective embodiments. A cyclotron chamber (accelerator chamber) R19 in which the cyclotron (particle accelerator) 2 is installed is formed on the second floor (top floor) of the building 6E, a first gantry chamber R20 in which the first rotating gantry 7 is installed is formed on the first floor, and a second gantry chamber R21 in which the second rotating gantry 8 is installed is formed in the first basement (bottom floor).

In the particle radiation therapy equipment 1E according to this embodiment, the cyclotron 2, the first rotating gantry 7, and the second rotating gantry 8 are installed on different floors of the building 6E, respectively. Accordingly, it may be possible to reduce as far as possible the installation area occupied by the equipment. As a result, it is easy to efficiently install the cyclotron 2, the first rotating gantry 7, and the second rotating gantry 8 at a predetermined site.

(Sixth Embodiment)

Figure 18:
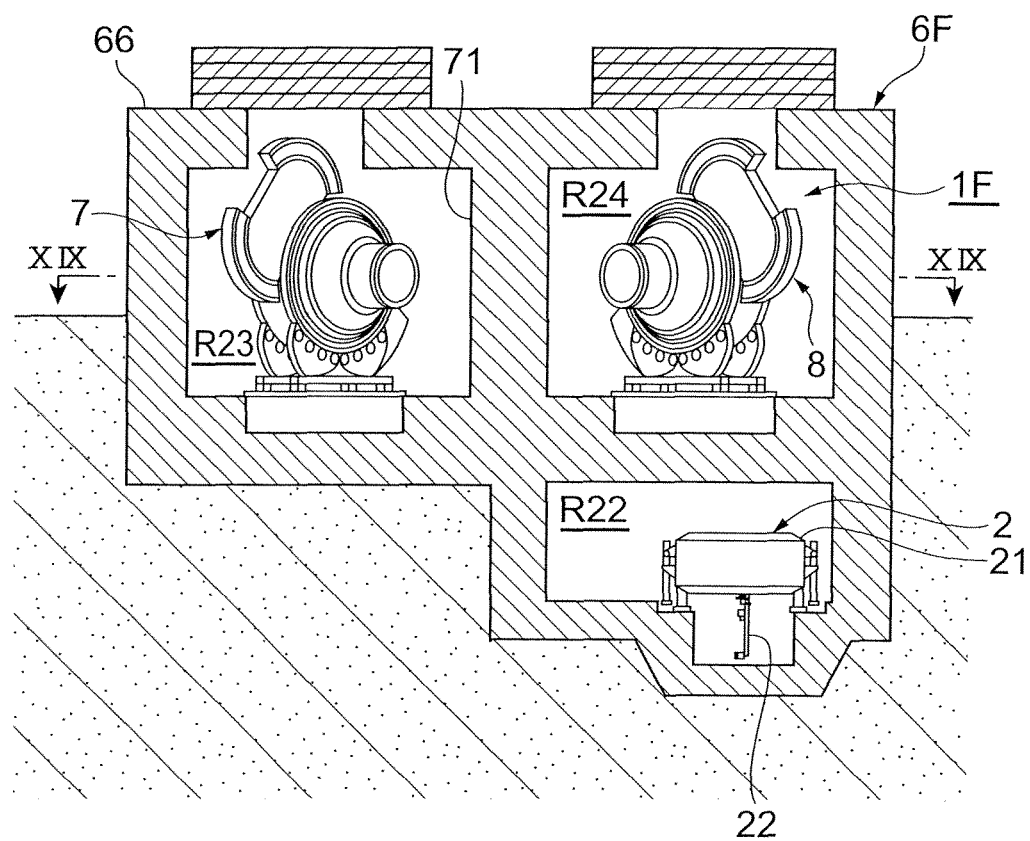
FIG. 18 is a side cross-sectional view of particle radiation therapy equipment according to a sixth embodiment of the invention.
Figure 19:
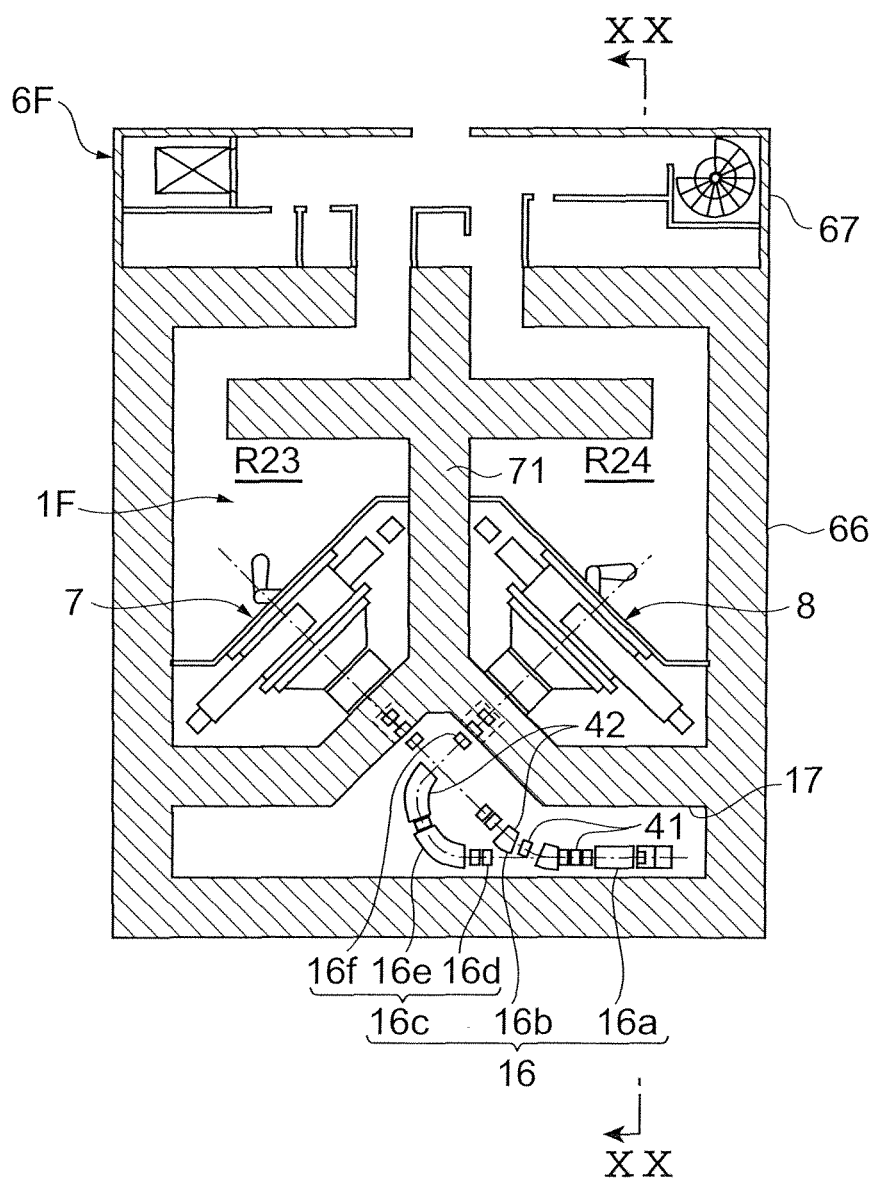
FIG. 19 is a cross-sectional view of a building taken along a line XIX-XIX of FIG. 18.
Figure 20:
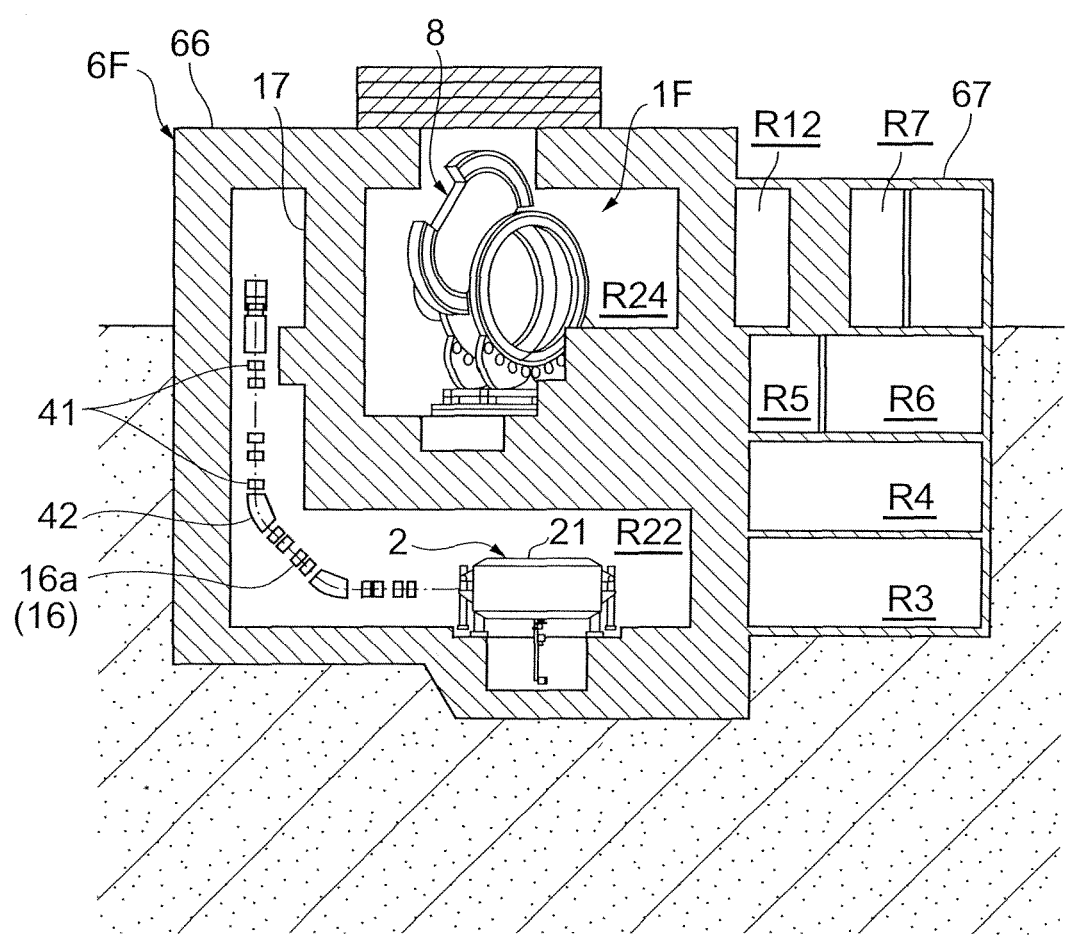
FIG. 20 is a cross-sectional view of a building taken along a line XX-XX of FIG. 19.

Next, particle radiation therapy equipment (accelerated particle irradiation equipment) 1F according to a sixth embodiment of the invention will be described with reference to FIGS. 18 to 20. Meanwhile, similar elements and members of the particle radiation therapy equipment 1F according to this embodiment to those of the pieces of particle radiation therapy equipment 1A to 1E according to the first to fifth embodiments are denoted by the same reference numerals, and a detailed description thereof will be omitted.

A building 6F of this embodiment is a building having, for example, a reinforced concrete structure or a steel skeleton concrete structure, and the respective chambers of the building are separated from each other by radiation shield walls made of concrete. Further, the building 6F includes a main building portion 66 and a sub-building portion 67. The sub-building portion 67 has a multi-story structure with three stories below and one story above the ground. A cooling device chamber R3, a power source chamber R4, a staff room R5, a radioactive material storage chamber R6, a treatment control room R7, and the like are formed on the respective floors.

The main building portion 66 has a multi-story structure with one story below and one story above the ground. A cyclotron (particle accelerator) 2 is installed in a cyclotron chamber (accelerator chamber) R22 that is formed in the first basement (bottom floor). First and second gantry chambers R23 and R24 are formed in parallel on the first floor, a first rotating gantry 7 is installed in the first gantry chamber R23, and a second rotating gantry 8 is installed in the second gantry chamber R24.

The first and second gantry chambers R23 and R24 are adjacent to each other with a radiation shield wall 71 interposed therebetween. The first gantry chamber R23 is formed in a substantially rectangular shape, and a labyrinthine passage R12 is formed on the front side of the first gantry chamber and communicates with a space in which a front desk, a patient waiting room, and the like are formed. The first rotating gantry 7 is disposed along a diagonal line of the first gantry chamber R23 formed in a substantially rectangular shape so that the front surface of the first rotating gantry faces the passage. The second gantry chamber R24 and the second rotating gantry 8 are symmetrical to the first gantry chamber R23 and the first rotating gantry 7 with the radiation shield wall 71 interposed therebetween.

A communication passage 17, through which a guide line 16 which forms the track of a proton beam passes, is formed on the rear side of the first and second rotating gantries 7 and 8. The guide line 16 includes a take-off path 16a, a first branched path 16b, and a second branched path 16c. The take-off path 16a communicates with the vacuum box 21 of the cyclotron 2, extends in the horizontal direction, is curved upward in the vertical direction at an angle of about 90°, passes through the communication passage 17, and is curved in the horizontal direction at an angle of about 90° on the first floor. The first and second branched paths 16b and 16c are branched from the take-off path 16a in two directions and communicate with the first and second rotating gantries 7 and 8, respectively.

The first branched path 16b is disposed on a horizontal plane and is connected to the first rotating gantry 7. The first branched path converges the proton beam and forms a predetermined curved track of the proton beam by the disposition of a plurality of quadrupole electromagnets 41 and deflecting electromagnets 42. The second branched path 16c is disposed on the same horizontal plane as the horizontal plane on which the first branched path 16b is disposed, and is connected to the second rotating gantry 8.

The second branched path 16c includes a branched portion 16d that is branched from the take-off path 16a and is separated from the first branched path 16b, a detour-intersection portion 16e that detours so as to be further separated from the second rotating gantry 8 than the first branched path 16b and intersects the first branched path 16b, and a connection portion 16f that is connected to the second rotating gantry 8 from the detour-intersection portion 16e.

The second branched path 16c requires a certain distance (the length of a path) in order to form a predetermined track that appropriately introduces a proton beam from take-off path 16a to the second rotating gantry 8. In the particle radiation therapy equipment 1F according to this embodiment, it may be possible to easily secure the length of the second branched path 16c by forming the detour-intersection portion 16e at the second branched path 16c without separating the first rotating gantry 7 from the second rotating gantry 8 in order to secure the length of the second branched path 16c. In addition, it may be possible to make the particle radiation therapy equipment compact by making the first and second branched paths 16b and 16c intersect each other. Accordingly, it may be possible to dispose the first and second rotating gantries so that the first rotating gantry 7 is as close as possible to the second rotating gantry 8. As a result, it is easy to efficiently install the first and second rotating gantries 7 and 8 at a predetermined site.

In the particle radiation therapy equipment 1F according to this embodiment, the cyclotron 2, the first rotating gantry 7, and the second rotating gantry 8 are installed on different floors of the building 6F, respectively. Accordingly, it may be possible to reduce as far as possible the installation area occupied by the equipment. As a result, it is easy to efficiently install the cyclotron 2 and the rotating gantries 7 and 8 at a predetermined site. In addition, since the cyclotron 2 is installed on the bottom floor of the building 6F, it is easy to increase the number of irradiation devices such as the rotating gantries 7 and 8.

Further, since the plurality of rotating gantries 7 and 8 is disposed on the same floor, that is, on the first floor in this embodiment, the particle radiation therapy equipment is effective when the height of the building 6F is not so high and the like.

Furthermore, since the second branched path 16c of the guide line 16 includes the detour-intersection portion 16e that detours so as to be further separated from the second rotating gantry 8 than the first branched path 16b and intersects the first branched path 16b, it may be possible to easily connect the second branched path to the second rotating gantry 8 adjacent to the first rotating gantry 7 while making the length of the second branched path 16c long.

Meanwhile, if the structure of the first and second branched paths 16b and 16c of the above-mentioned guide line 16 is employed, it may be possible to efficiently install the cyclotron and the plurality of irradiation devices at a predetermined site even though all the cyclotron (particle accelerator) and the plurality of irradiation devices are installed on the same floor of the building. For example, the first and second branched paths 16b and 16c branched from the take-off path 16a connected to the vacuum box 21 of the cyclotron 2 are disposed on the same floor, the first branched path 16b is connected to the first rotating gantry 7, and the second branched path 16c is connected to the second rotating gantry 8. In this case, since the second branched path 16c includes the detour-intersection portion 16e, it is easy to secure the length of the second branched path 16c. In addition, since the first and second branched paths 16b and 16c intersect each other, it may be possible to easily make the particle radiation therapy equipment compact.

(Seventh Embodiment)

Figure 21:
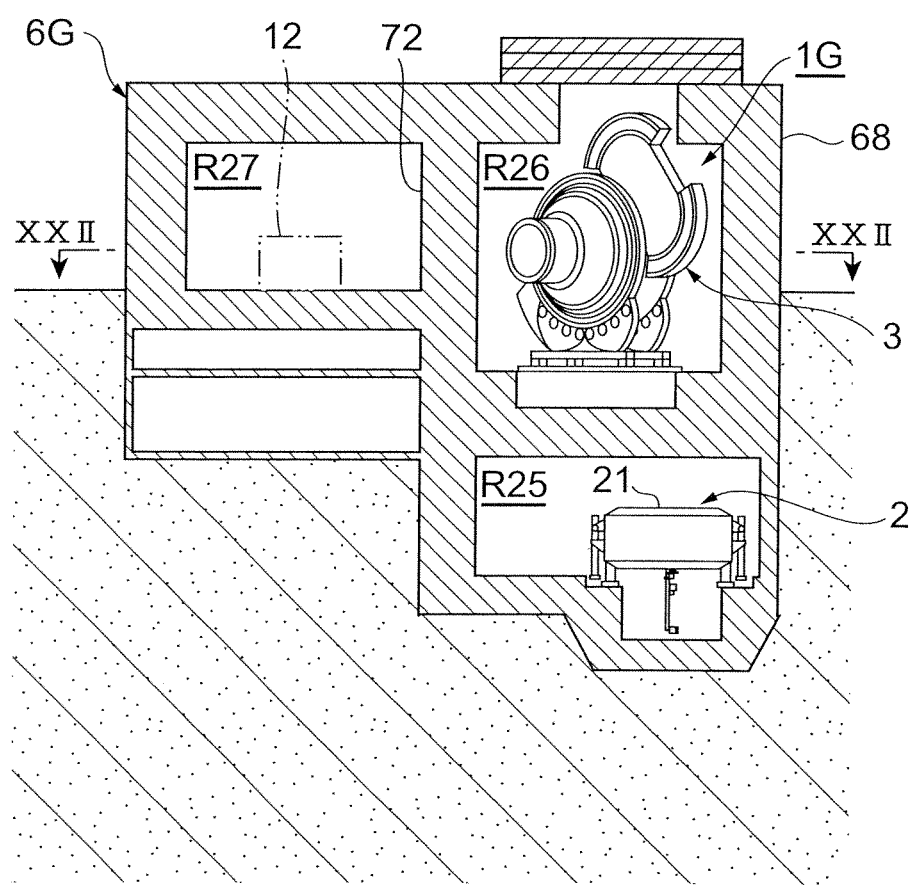
FIG. 21 is a side cross-sectional view of particle radiation therapy equipment according to a seventh embodiment.
Figure 22:
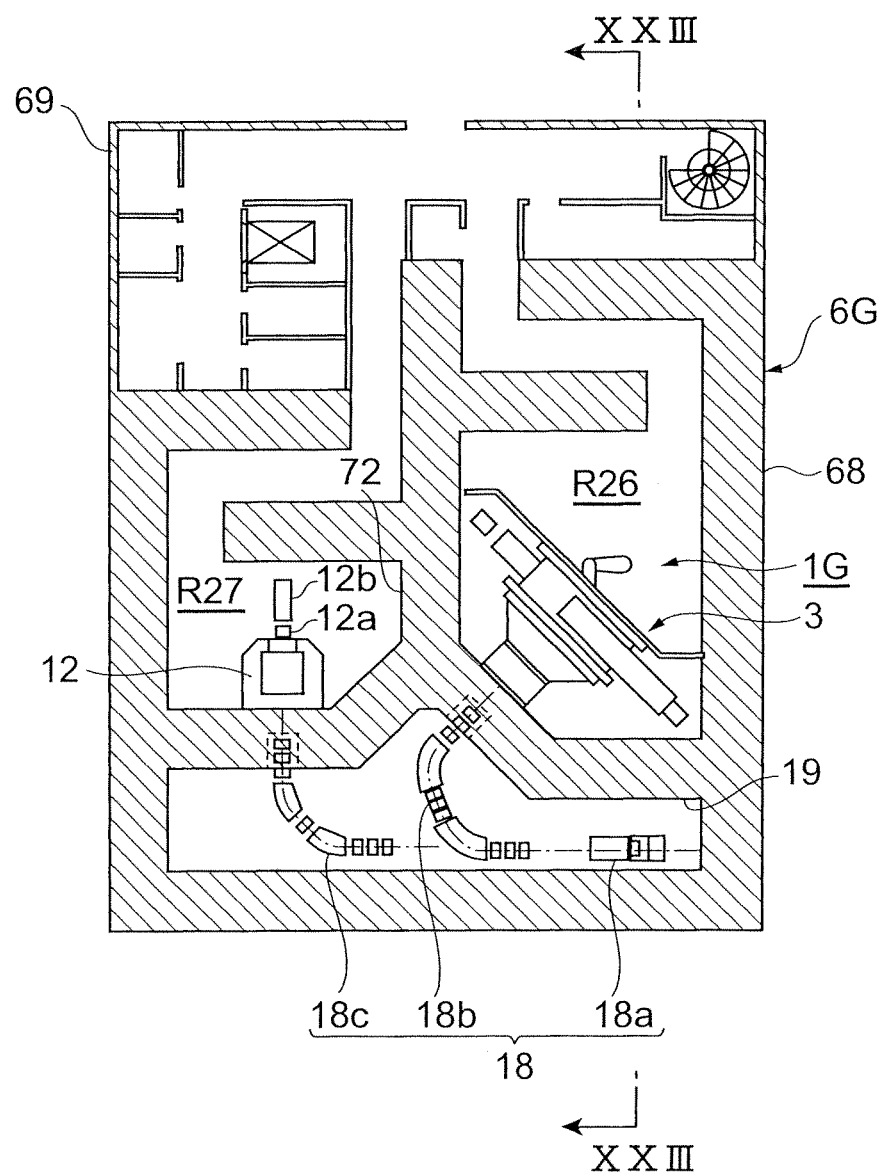
FIG. 22 is a cross-sectional view of a building taken along a line XXII-XXII of FIG. 21.
Figure 23:
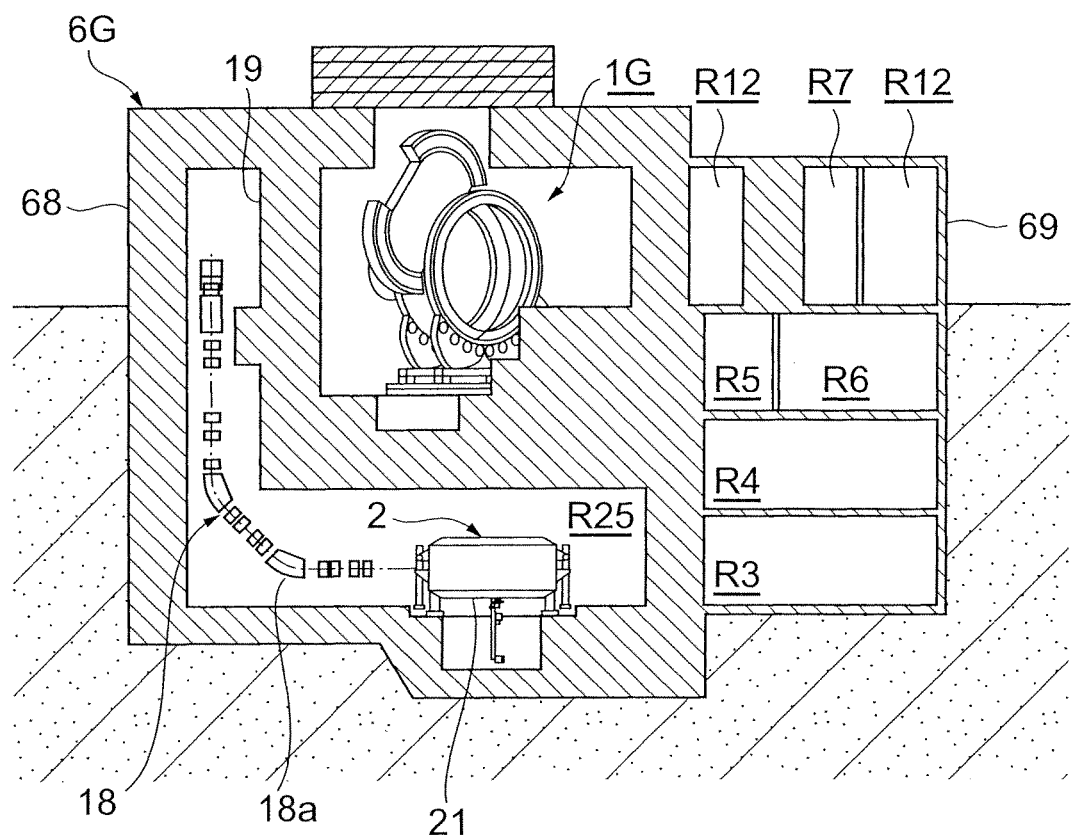
FIG. 23 is a cross-sectional view of a building taken along a line XXIII-XXIII of FIG. 22.

Next, particle radiation therapy equipment (accelerated particle irradiation equipment) 1G according to a seventh embodiment of the invention will be described with reference to FIGS. 21 to 23. Meanwhile, similar elements and members of the particle radiation therapy equipment 1G according to this embodiment to those of the pieces of particle radiation therapy equipment 1A to 1F according to the first to sixth embodiments are denoted by the same reference numerals, and a detailed description thereof will be omitted.

A building 6G of this embodiment is a building having, for example, a reinforced concrete structure or a steel skeleton concrete structure, and the respective chambers of the building are separated from each other by radiation shield walls made of concrete. Further, the building 6G includes a main building portion 68 and a sub-building portion 69. The sub-building portion 69 has a multi-story structure with three stories below and one story above the ground. A cooling device chamber R3, a power source chamber R4, a staff room R5, a radioactive material storage chamber R6, a treatment control room R7, and the like are formed on the respective floors.

The main building portion 68 has a multi-story structure with one story below and one story above the ground. A cyclotron (particle accelerator) 2 is installed in a cyclotron chamber (accelerator chamber) R25 that is formed in the first basement (bottom floor). A gantry chamber R26 and a stationary irradiation chamber R27 are formed in parallel on the first floor, a rotating gantry 3 is installed in the gantry chamber R26, and a stationary irradiation device 12 is installed in the stationary irradiation chamber R27.

The gantry chamber R26 and the stationary irradiation chamber R27 are adjacent to each other with a radiation shield wall 72 interposed therebetween. Further, a communication passage 19 through which a guide line 18 passes is formed adjacent to the gantry chamber R26 and the stationary irradiation chamber R27. The guide line 18 includes a take-off path 18a, a first branched path 18b, and a second branched path 18c. The take-off path 18a communicates with a vacuum box 21 of the cyclotron 2, extends in the horizontal direction, is curved upward in the vertical direction at an angle of about 90°, passes through the communication passage 19, and is curved in the horizontal direction at an angle of about 90° on the first floor. The first and second branched paths 18b and 18c are branched from the take-off path in two directions and communicate with the rotating gantry 3 and the stationary irradiation device 12, respectively.

In the particle radiation therapy equipment according to this embodiment, the cyclotron, the rotating gantry, and the stationary irradiation device are installed on different floors of the building, respectively. Accordingly, it may be possible to reduce as far as possible the installation area occupied by the equipment. As a result, it is easy to efficiently install the cyclotron, the rotating gantry, and the stationary irradiation device at a predetermined site. Further, since the cyclotron is installed on the bottom floor of the building, it is easy to increase the number of irradiation devices such as the rotating gantry. Furthermore, it may be possible to separately use the rotating gantry and the stationary irradiation device in this embodiment, so that the particle radiation therapy equipment is effective for appropriately irradiating a patient with a proton beam.

The invention has been specifically described above with reference to the embodiments, but the invention is not limited to the above-mentioned embodiments. In the above-mentioned embodiments, the plurality of rotating gantries has been installed as a plurality of irradiation devices and the rotating gantry and the stationary irradiation device have been installed as a plurality of irradiation devices. However, the particle radiation therapy equipment may include a plurality of stationary irradiation devices. Further, the particle accelerator is not limited to a cyclotron, and may be a synchrotron or a synchrocyclotron. Furthermore, particle radiation (accelerated particle) is not limited to a proton beam and may be a carbon beam (baryon beam).

It should be understood that the invention is not limited to the above-described embodiments, but may be modified into various forms on the basis of the spirit of the invention. Additionally, the modifications are included in the scope of the invention.

What is claimed is:

1. Particle radiation therapy equipment comprising:
    a particle accelerator configured to generate accelerated particles;
    a rotating gantry having a rotating unit and an irradiation unit, the rotating unit is rotatable about a rotation axis, the irradiation unit is disposed on the rotating unit and irradiates the accelerated particles;
    a guide line configured to guide the accelerated particles generated by the particle accelerator to the rotating gantry; and
    a building having a main building portion and a sub-building portion disposed adjacent to the main building portion in a lateral direction, both the main building portion and the sub-building portion have a multi-story structure with a plurality of stories continuing in a vertical direction with respect to each other, wherein the main building portion has a wall portion which is thicker than that of the sub-building portion,
    wherein the main building portion has an accelerator chamber and a gantry chamber, the particle accelerator is installed in the accelerator chamber and the rotating gantry is installed in the gantry chamber, the main building portion having the guide line installed therein,
    wherein the gantry chamber is installed on at least one of upper and lower floors of a floor on which the accelerator chamber is installed, and
    wherein the sub-building portion includes a power source chamber, and a power-supply equipment is disposed in the power source chamber.

2. The particle radiation therapy equipment according to claim 1,
    wherein the accelerator chamber is located on a basement floor, and the gantry chamber is located on an above-ground floor.

3. The particle radiation therapy equipment according to claim 2, wherein the gantry chamber is only located on a first floor.

4. The particle radiation therapy equipment according to claim 1, wherein the guide line is only disposed on a virtual plane extending in the vertical direction.

5. The particle radiation therapy equipment according to claim 4, wherein the guide line is connected with the particle accelerator at a terminal portion thereof, is connected with the rotating gantry at another terminal portion thereof, and from the terminal portion to the another terminal portion is only disposed on the virtual plane.

6. The particle radiation therapy equipment according to claim 1, wherein the rotating gantry has an introduction line configured to introduce the accelerated particles guided by the guide line to the irradiation unit, and the introduction line is curved at an angle of 90° with respect to the rotation axis from a start end portion thereof communicating with the guide line and extends in a radial direction of the rotating unit, is curved at an angle of 135° in a circumferential direction of the rotating unit and extends, and is curved toward an inside in the radial direction at an angle of 135° and communicates with the irradiation unit at a terminal end portion thereof.

7. The particle radiation therapy equipment according to claim 1, wherein the particle accelerator is not installed in the gantry chamber and the rotating gantry is not installed in the accelerator chamber.

* * * * *